(12) United States Patent
Wright

(10) Patent No.: US 10,405,870 B2
(45) Date of Patent: Sep. 10, 2019

(54) FASTENER APPARATUS FOR TISSUE AND METHODS OF DEPLOYMENT AND MANUFACTURE

(71) Applicant: David W. Wright, Littleton, CO (US)

(72) Inventor: David W. Wright, Littleton, CO (US)

(*) Notice: Subject to any disclaimer, the term of this patent is extended or adjusted under 35 U.S.C. 154(b) by 86 days.

(21) Appl. No.: 15/330,854

(22) Filed: Nov. 7, 2016

(65) Prior Publication Data
US 2017/0164950 A1     Jun. 15, 2017

Related U.S. Application Data

(62) Division of application No. 11/237,132, filed on Sep. 27, 2005, now Pat. No. 9,486,216.

(60) Provisional application No. 60/613,434, filed on Sep. 27, 2004.

(51) Int. Cl.
| | |
|---|---|
| *A61B 17/128* | (2006.01) |
| *A61B 17/11* | (2006.01) |
| *A61B 17/122* | (2006.01) |
| *A61B 17/072* | (2006.01) |
| *A61B 17/115* | (2006.01) |
| *A61B 17/00* | (2006.01) |

(52) U.S. Cl.
CPC ......... *A61B 17/128* (2013.01); *A61B 17/072* (2013.01); *A61B 17/11* (2013.01); *A61B 17/122* (2013.01); *A61B 17/115* (2013.01); *A61B 2017/00243* (2013.01); *A61B 2017/1107* (2013.01); *A61B 2017/1139* (2013.01)

(58) Field of Classification Search
CPC ..... A61B 17/128; A61B 17/072; A61B 17/11; A61B 17/122; A61B 17/115; A61B 2017/00243; A61B 2017/1107; A61B 2017/1139
See application file for complete search history.

(56) References Cited

U.S. PATENT DOCUMENTS

| | | | | |
|---|---|---|---|---|
| 5,234,447 | A | * | 8/1993 | Kaster ............. A61B 17/11 606/151 |
| 5,868,763 | A | * | 2/1999 | Spence ............ A61B 17/11 606/139 |
| 6,113,612 | A | * | 9/2000 | Swanson ........... A61F 2/88 623/1.15 |

(Continued)

*Primary Examiner* — Jing Rui Ou
(74) *Attorney, Agent, or Firm* — John D. Wright; Dickinson Wright PLLC

(57) ABSTRACT

An apparatus and method for connecting two tubular vessels together in a side-by-side or tangential manner is disclosed. The apparatus has an annulus and at least one series of fingers connected to and extending away from the annulus. Each finger is preferably heat-formed into an arcuate shape. In use, a deployment apparatus is used to constrain the fingers of the apparatus to be in a relatively planar configuration. The deployment apparatus containing the apparatus is placed between and in contact with the two tubular vessels so that one tubular vessel is above the device and one tubular vessel is below the device and so that the fingers of the device come into contact with the tissue of the vessels. As the fingers penetrate the vessels the constraint on the fingers is removed so that the fingers can assume their unbiased, heat-formed arcuate shape. In this way, the fingers penetrate and grasp the tissue of the vessels so that the apparatus grasps the vessels and pulls the vessels toward each other.

4 Claims, 33 Drawing Sheets

(56) References Cited

U.S. PATENT DOCUMENTS

| | | | | |
|---|---|---|---|---|
| 6,179,849 | B1* | 1/2001 | Yencho | A61B 17/11 606/153 |
| 6,391,036 | B1* | 5/2002 | Berg | A61B 17/0057 606/151 |
| 6,616,675 | B1* | 9/2003 | Evard | A61B 1/3137 606/153 |
| 6,811,555 | B1* | 11/2004 | Willis | A61B 17/11 606/151 |
| 2001/0044631 | A1* | 11/2001 | Akin | A61B 17/11 606/153 |
| 2002/0082627 | A1* | 6/2002 | Berg | A61B 17/0057 606/155 |
| 2002/0091398 | A1* | 7/2002 | Galdonik | A61B 17/11 606/153 |
| 2002/0169466 | A1* | 11/2002 | Peterson | A61B 17/064 606/153 |
| 2003/0045902 | A1* | 3/2003 | Weadock | A61B 17/11 606/219 |
| 2003/0088256 | A1* | 5/2003 | Conston | A61B 17/11 606/155 |
| 2003/0120292 | A1* | 6/2003 | Park | A61B 17/083 606/153 |

* cited by examiner

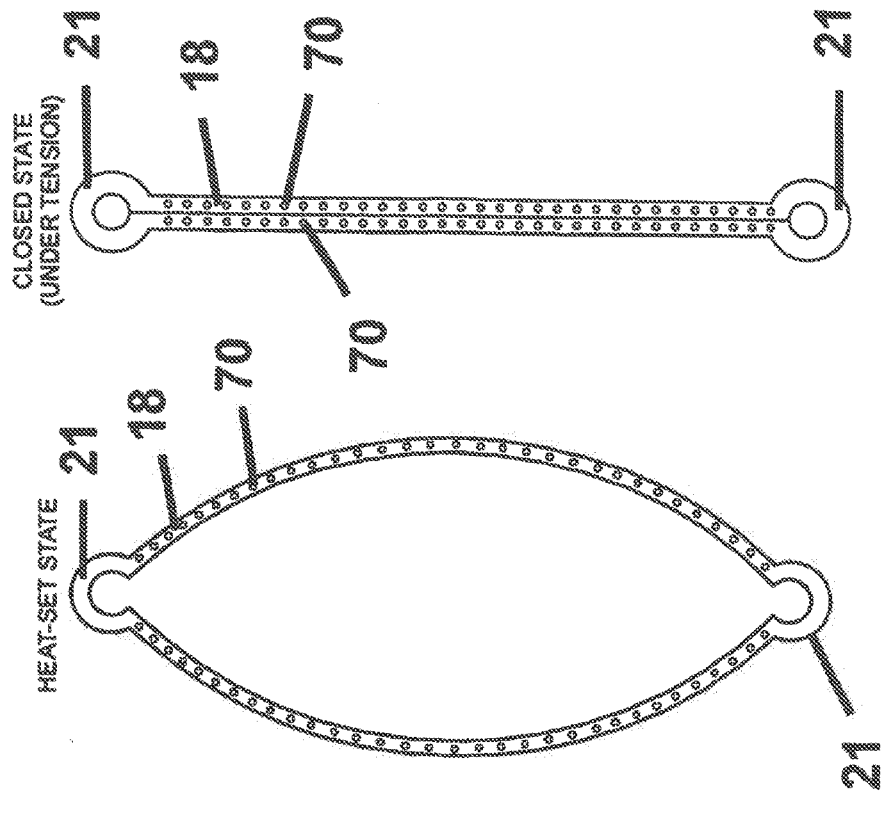

FLAT STOCK RECEIVING WIRE SEGMENTS

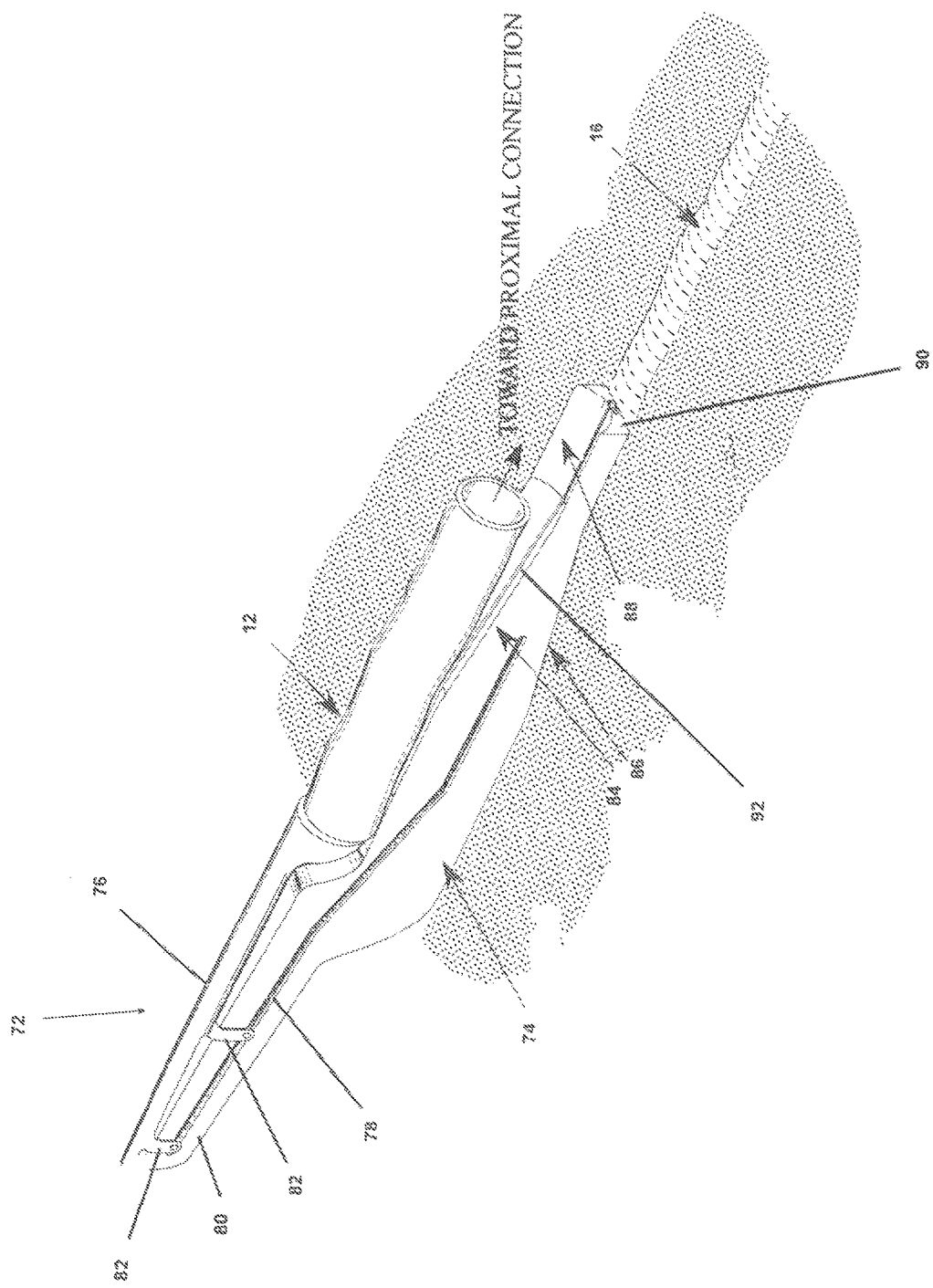

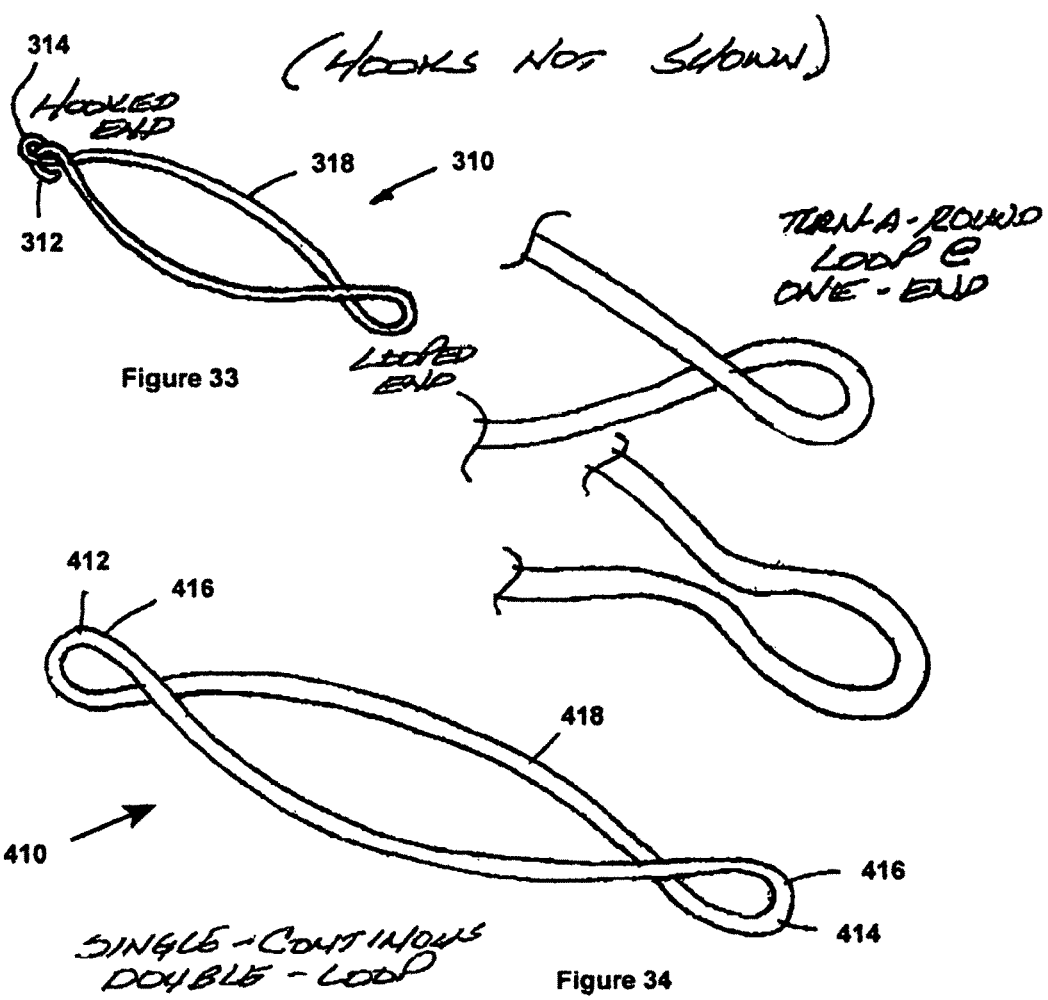

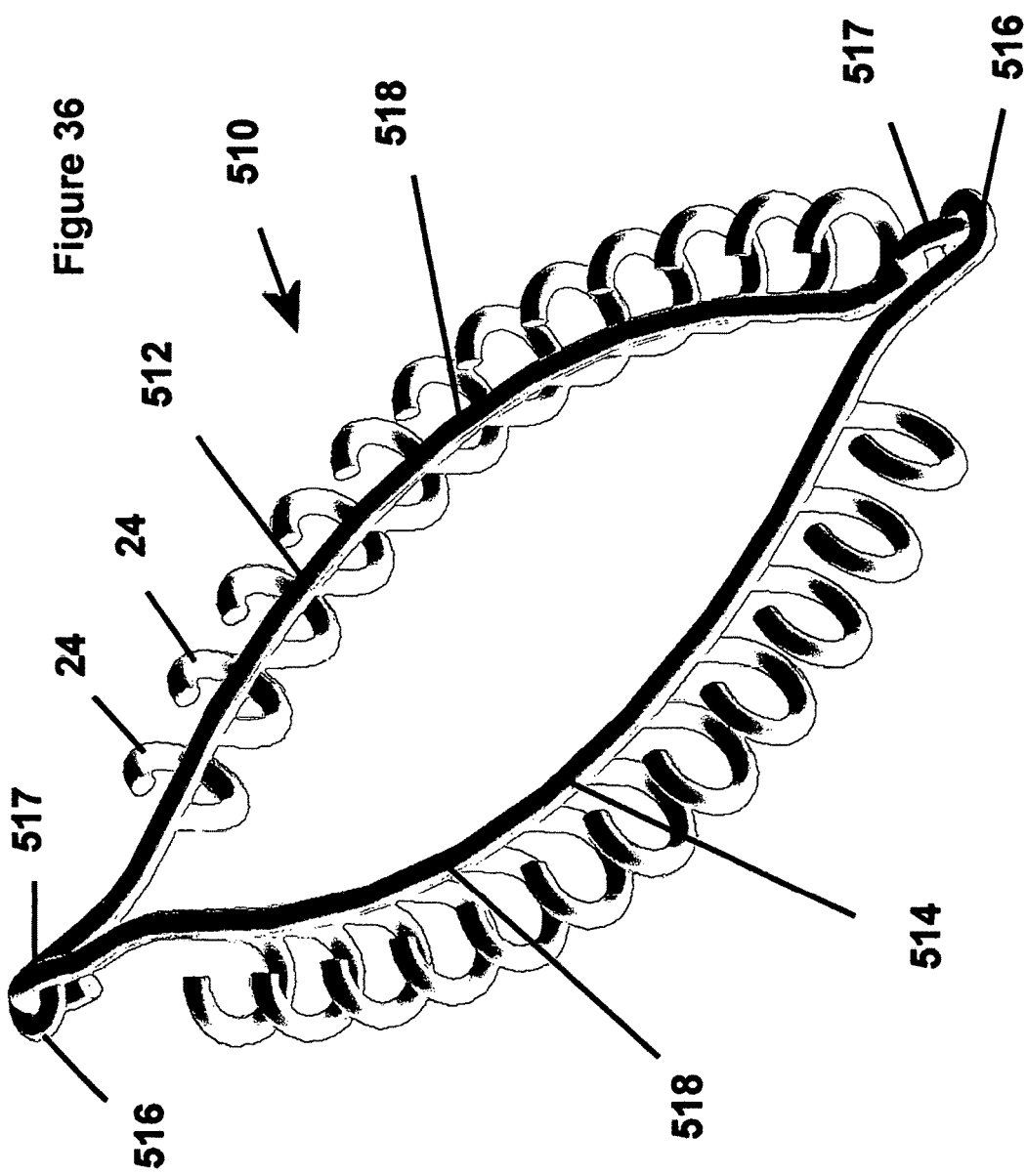

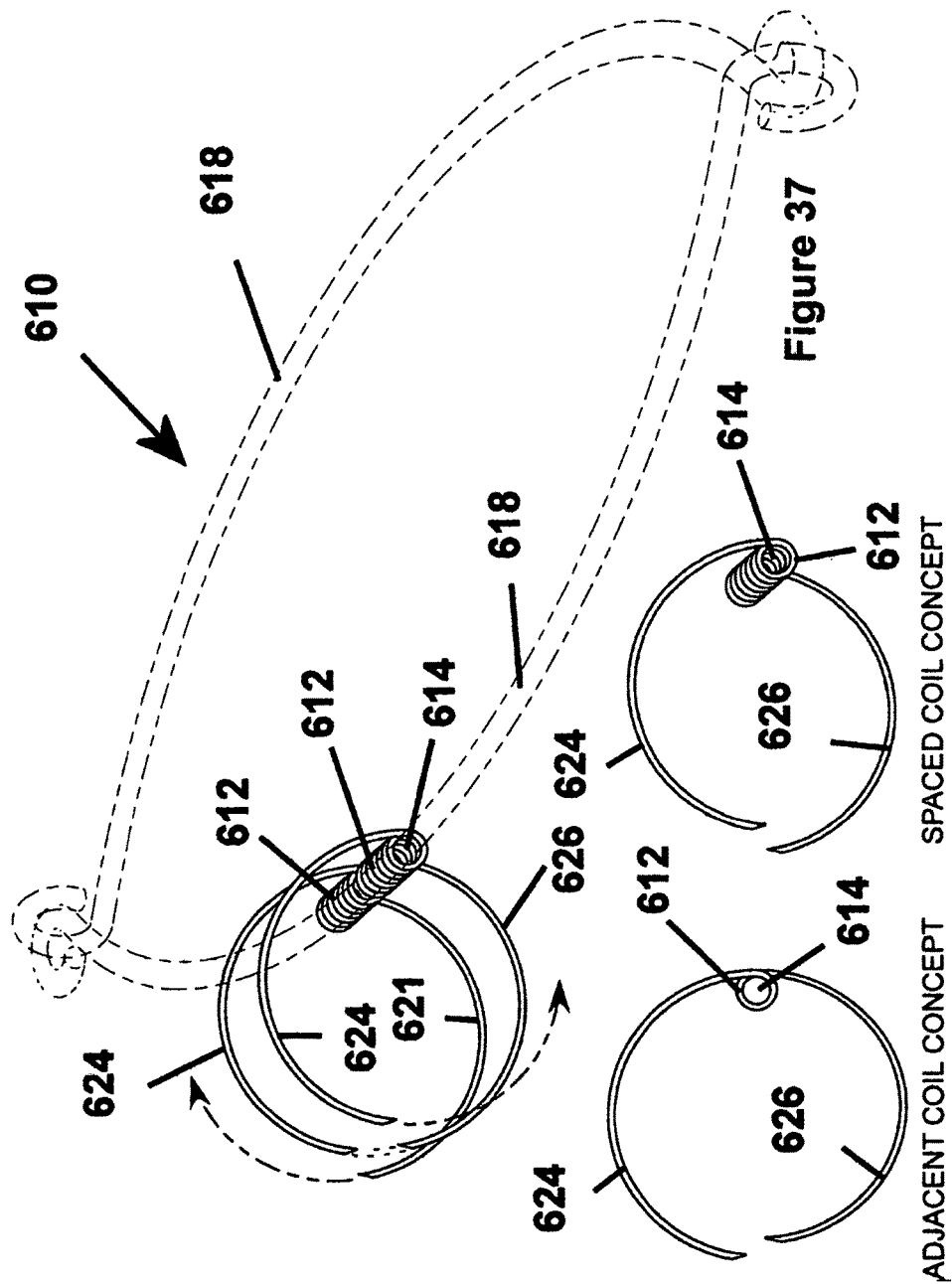

FASTENER APPARATUS FOR TISSUE AND METHODS OF DEPLOYMENT AND MANUFACTURE

CROSS REFERENCE TO RELATED APPLICATION

This divisional application claims priority to U.S. application Ser. No. 11/237,132, filed Sep. 27, 2005, issued on Nov. 8, 2016 as U.S. Pat. No. 9,486,216, which claims the benefit of U.S. Provisional Application Ser. No. 60/613,434, filed Sep. 27, 2004, which are all incorporated herein by reference in their entirety.

BACKGROUND OF THE INVENTION

1. Field of the Invention

This invention relates generally to methods and devices for surgically joining separate pieces of tissue to one another, and more particularly to surgically joining a tubular graft of tissue to a separate piece of tissue.

2. Related Art

In performing bypass surgery, it is a known practice to repair a clogged or an otherwise damaged segment of tubular tissue, for example a coronary artery, by attaching a healthy section of artery, for example, a mammary artery, to the tubular tissue below the clog or damaged segment so that blood flows from the healthy section of artery into the tubular tissue below the clogged or damaged segment. In addition, it is also known to bypass a clogged or damaged section of artery (e.g., a coronary artery) by forming a graft made of a section of vein harvested from elsewhere (e.g., a Saphenous vein harvested from the thigh) extending from the aorta to a section of the clogged or damaged artery beyond the clog or damage. The resulting graft is known as a Coronary Artery Bypass Graft (CABG—pronounced "cabbage") and the procedure to form the graft is known as a CABG procedure.

While performing the procedures mentioned above, a surgeon ordinarily will perform a sternectomy, a procedure to open the patient's chest to provide access to the patient's heart. Thereafter, the patient is typically put on a bypass system that performs the function of the patient's own heart and lungs as well as cools and warms the patient's blood. As the patient is put on the bypass system, the patient's heart is stopped or "arrested" so that the surgeon may perform the CABG procedure.

It is important that each end of the CABG graft is well attached to the aorta or coronary artery, respectively. This is necessary in order to provide a leak-proof anastomosis and also to allow the tissue to heal together into a strong, leak-proof connection. This connection is generally done by the surgeon making numerous stitches of suture (typically 6-8 on each end of the graft) between the vessel and the tissue that the graft is being joined to. In some cases, the surgeon must replace sutures that do not create a leak-proof anastomosis between the pieces of tissue. After the CABG procedure is complete, the patient is taken off the bypass system, the patient's heart allowed to restart and the patient's chest closed.

The entire procedure is ordinarily quite exhausting and requires a long time to complete the procedure, generally ranging between 2 to 6 hours or more. Statistically, 3-7% of patients that are put on a bypass system experience some form of neurological complications. The longer the patient is on the bypass system, the more likely he or she is to experience such complications. It typically takes a surgeon between 6-12 minutes to attach each end of the graft to the aorta and coronary artery, respectively. Much of the surgeon's time is spent making certain that the segments of tissue are joined together in a leak-proof anastomosis. Generally, this requires the surgeon to make numerous stitches of suture between the segments of tissue being joined to one another, and in some cases replacing sutures that do not create a leak-proof anastomosis between the pieces of tissue.

Though using sutures to join segments of tissue to one another in open heart surgery, or other forms of surgery, has proven successful, not only does it require a longer than desirable amount of time in surgery, there is also a danger of the suture becoming damaged. Damage to a portion of the suture may occur in many ways, such as through inadvertent grasping or clamping by a surgical instrument or through nicking a suture with the needle as an adjacent suture is installed. Ordinarily, a damaged piece of suture has a substantially reduced tensile strength and thus may ultimately fail to maintain the pieces of tissue joined to one another.

SUMMARY OF THE INVENTION

In accordance with one aspect of the invention, a device for connecting two tubular vessels together in a side-by-side or tangential manner is disclosed. The device has an annulus and at least one series of fingers connected to and extending away from the annulus. In the preferred embodiment there are two sets of fingers connected to and extending away from the annulus in opposite directions. Each finger is preferably biased into an arcuate shape.

In use, a deployment apparatus is used to constrain the fingers of the device to be in a relatively planar configuration. The deployment apparatus containing the device is placed between and in contact with the two tubular vessels so that one tubular vessel is above the device and one tubular vessel is below the device and so that the fingers of the device come into contact with the tissue of the vessels. As the fingers penetrate the vessels the constraint on the fingers is removed so that the fingers can assume their unbiased arcuate, heat-shaped configuration. In this way, the fingers penetrate and grasp the tissue of the vessels so that the device grasps the vessels and pulls the vessels toward each other. After the device is deployed in the tissue of the vessels so that the fingers enter into and grasp the tissue, a cutting surface cuts the tissue between the fingers thereby forming an opening from one vessel through the device to the other vessel.

An object, feature or advantage of this invention, in one or more embodiments of the invention, is to provide an apparatus and method of deployment that provides a secure and reliable side anastomosis between a tubular duct and a wall of a vessel.

Another object, feature or advantage of this invention, in one or more embodiments of the invention, is to provide an apparatus and method of deployment that establishes a quick biocompatible bond between mating tissues.

Another object, feature or advantage of this invention, in one or more embodiments of the invention, is to provide an apparatus and method of deployment that imparts a biasing force to maintain connected tissues in abutting contact with one another.

Another object, feature or advantage of this invention, in one or more embodiments of the invention, is to provide an apparatus and method of deployment that readily penetrates tissue without damaging the tissue.

Another object, feature or advantage of this invention, in one or more embodiments of the invention, is to provide an apparatus and method of deployment that provides a quick and reliable mechanism in which to attach separate tissues to one another.

Another object, feature or advantage of this invention, in one or more embodiments of the invention, is to provide an apparatus and method of deployment that is of relatively simple design and is economical in manufacture and assembly and is efficient in use.

In accordance with another aspect of the invention, an apparatus for securing a tubular duct having a wall to a vessel having a wall in a side by side configuration includes a circumferentially continuous annulus having a first set of fingers extending from the annulus in a first direction. The first set of fingers are configured for automatic movement from a first biased configuration toward an unbiased, heat-formed, relaxed second configuration. The first set of fingers is configured to penetrate and grasp the wall of either the tubular duct or vessel as they move from the first configuration toward the second configuration.

In accordance with yet another aspect of the invention, the apparatus can include a second set of fingers extending at least in part from the annulus in a second direction generally opposite the first direction of the first set of fingers. The second set of fingers is configured for automatic movement from a first biased configuration toward an unbiased, heat-formed, second relaxed configuration. The second set of fingers is configured to penetrate and grasp the other of the wall of either the tubular duct or vessel as they move from the first configuration toward the second configuration, where the first and second sets of fingers penetrate opposite ones of the wall of the tubular duct and the vessel.

In accordance with yet another aspect of the invention, a method for deploying a fastener to secure a tubular duct having a wall to a vessel having a wall in a side-by-side configuration is provided. The method includes constraining a first set of fingers of the fastener with a deployment apparatus to move the first set of fingers into a biased state; disposing the constrained fastener between the tubular duct and vessel; and releasing the constrained fastener from the deployment tool to allow the first set of fingers to assume a relaxed, unbiased shape and penetrate and grasp at least one of the tubular duct and vessel so that the fastener grasps and fixes the tubular duct and vessel to each other.

In accordance with yet another aspect of the invention, the method can further include forming an opening within at least one of the tubular duct and vessel to allow blood to flow through the opening by extending a cutting member on the deployment tool between the first set of fingers and cutting tissue of at least one of the tubular duct and vessel with the cutting member.

In accordance with yet another aspect of the invention, the method can further include constraining a second set of fingers of the fastener with the deployment apparatus to move the second set of fingers into a biased state and allowing the second set of fingers to assume a relaxed, unbiased shape and penetrate and grasp at least one of the tubular duct and vessel upon releasing the constrained fastener from the deployment tool.

In accordance with yet another aspect of the invention, the method can further include biasing the first and second sets of fingers into a substantially coplanar relation with one another while constraining the first and second sets of fingers with the deployment tool.

In accordance with yet another aspect of the invention, the method can further include allowing the first and second sets of fingers to take on an arcuate heat-shaped, relaxed configuration upon releasing the constrained fastener from the deployment tool.

BRIEF DESCRIPTION OF THE DRAWINGS

These and other objects, features and advantages of this invention will become apparent from the following detailed description of the preferred embodiments and best mode, appended claims and accompanying drawings in which:

FIG. 6 is a plan view of an annulus of a fastener apparatus constructed according to another embodiment of the invention shown in a preformed state of construction;

FIG. 7 is a plan view of the annulus of FIG. 6 in a heat set form and shown in an unbiased state;

FIG. 8 is a plan view of the annulus of FIG. 6 in a closed or under-tension state;

FIG. 11 is a perspective view of a deployment apparatus with a tubular duct received thereon overlying another tubular duct within a vessel;

FIG. 33 is a schematic view of another embodiment of an annulus for a fastener apparatus according to another embodiment of the invention;

FIG. 34 is a schematic view of another embodiment of an annulus for a fastener apparatus according to another embodiment of the invention;

FIG. 36 is a partial top view of the fastener apparatus of FIG. 35; and

FIG. 37 is a schematic perspective view of yet another embodiment of a fastener apparatus constructed according to another embodiment of the invention.

DETAILED DESCRIPTION OF THE PREFERRED EMBODIMENTS

Figure 1:
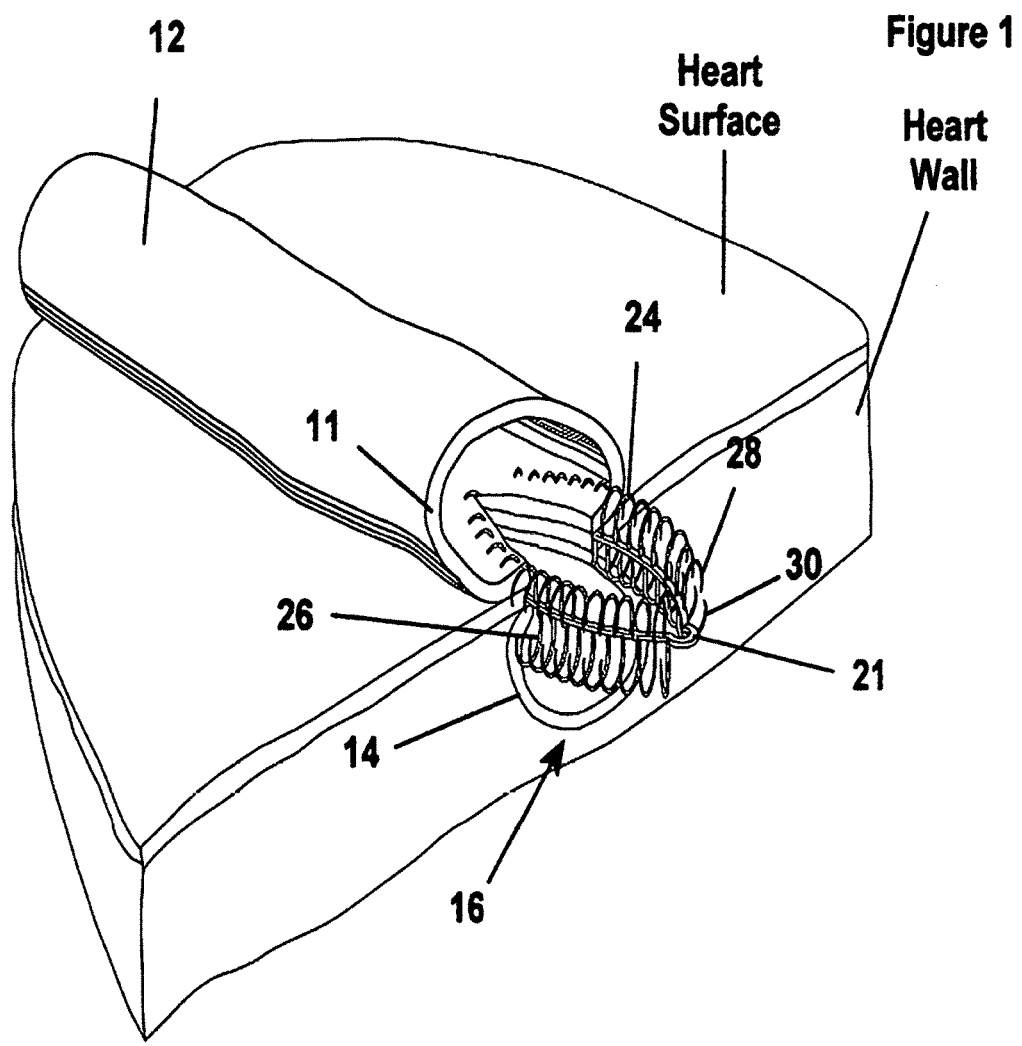
FIG. 1 is a broken away perspective view showing a fastener apparatus constructed according to one presently preferred embodiment of the invention attaching the tubular graft to the heart wall providing a blood flow path between the tubular graft and the artery underlying the heart wall.

Referring to FIG. 1, an apparatus, referred to hereafter as a fastener 10, is shown making a generally tangential anastomosis between two pieces of tissue, represented here as a wall 11 of a generally tubular duct 12, for example and without limitation, a graft of an artery or vein, and a wall 14 of a vessel 16, for example and without limitation, a wall forming a coronary artery. The anastomosis established by the fastener 10 provides a sutureless connection between a wall 11 of the tubular duct 12 and the wall 14 of a vessel 16, thereby facilitating making a tangential connection between the duct 12 and the vessel 16. Desirably, the fastener 10 biases the tubular duct 12 and the wall 14 of the vessel 16 toward one another, thereby establishing a leakproof attachment between the tubular duct 12 and the vessel 16. Additionally, the continual bias imparted by the fastener 10 between the tubular duct 12 and the wall 14 of the vessel 16 facilitates the formation of a biological bond between the tubular duct 12 and the vessel 16 as the patent heals after the CABG procedure.

Figure 2:
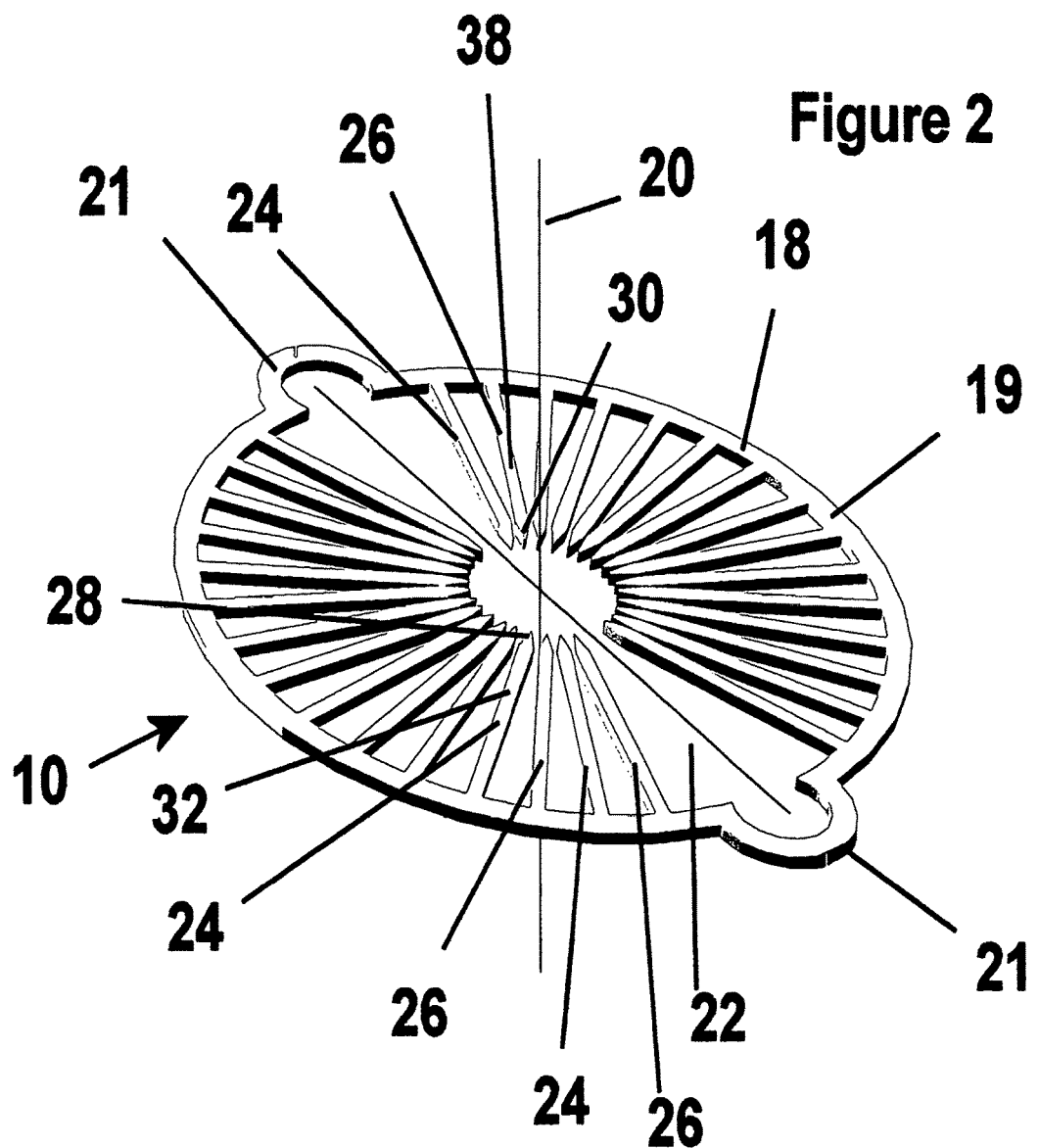
FIG. 2 is a perspective view of the fastener apparatus of FIG. 1 in a preformed state of construction.
Figure 3:
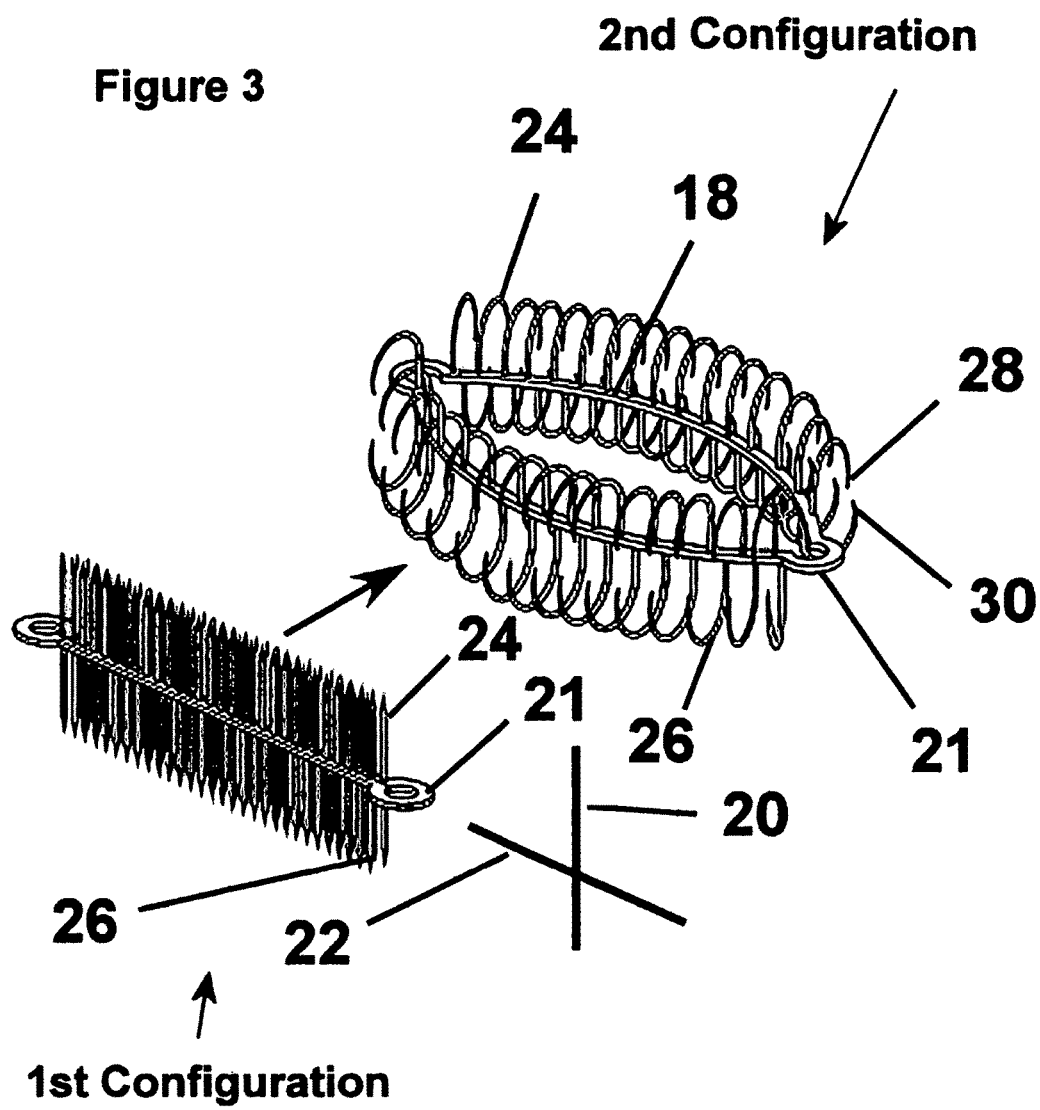
FIG. 3 is a perspective view of the fastener apparatus of FIG. 1 in first and a second configuration.

Referring to FIGS. 1-3, the fastener 10 has an annulus 18 with a perpendicular axis 20 and a longitudinal axis 22. The annulus 18 has a flange 19 with a first set of fingers 24 and a second set of fingers 26. Fingers 24, 26 extend away from the annulus 18. In the preformed state of construction shown in FIG. 2, the fingers 24, 26 extend radially inward from the annulus 18. However, as shown in the 1.sup.st configuration of FIG. 3, fingers 24, 26 are biased to extend away from annulus 18 generally in opposite directions from the annulus 18 and in a relatively planar fashion, prior to the fingers 24, 26 taking on a generally arcuate, curved, or hook shaped configuration. Further, as shown in the 2.sup.nd configuration of FIG. 3, the first set of fingers 24 are biased to extend generally axially from the annulus 18 in one direction to a 180 degree bend extending generally radially outwardly from the perpendicular axis 20, thereafter, leading to free ends 28. In addition, as shown in the 2.sup.nd configuration of FIG. 3, the second set of fingers 26 are biased to extend generally axially from the annulus 18 in another direction generally opposite the direction of the first set of fingers 24 to a 180 degree bend extending generally radially outwardly from the perpendicular axis 20, thereafter, leading to free ends 30.

In a relaxed condition shown in the 2.sup.nd configuration of FIG. 3, the annulus 18 generally remains generally oval in form, while also in a relaxed condition, the bends in the respective sets of fingers 24, 26, define the generally arcuate, or curved portions of the fastener 10 that define a generally C-shaped fastener in axial cross-section. It should be recognized that the fingers 24, 26, and annulus 18 may be formed having different geometries than described above, for example, instead of the fingers 24, 26 having a continuous arcuate shape in their relaxed configuration, fingers 24, 26 may have a plurality of stepped linear sections defining the generally hook shaped configuration.

The first set of fingers 24 are moveable or bendable between a first, extended or biased, generally linear or at least partially flattened configuration (FIG. 21) and a second, retracted or unbiased, at least partially arcuate, hook shaped, curled or otherwise nonlinear configuration (FIGS. 1 and 28) extending at least in part generally radially outwardly from the perpendicular axis 20 to penetrate the tissue, in use. The second set of fingers 26 are moveable or bendable between a first, extended or biased, generally linear or at least partially flattened configuration and a second, retracted or unbiased, at least partially arcuate, hook shaped, curled or otherwise nonlinear configuration (FIGS. 1 and 28) extending at least in part generally radially outwardly from the perpendicular axis 20 to penetrate the tissue, in use.

Figure 21:
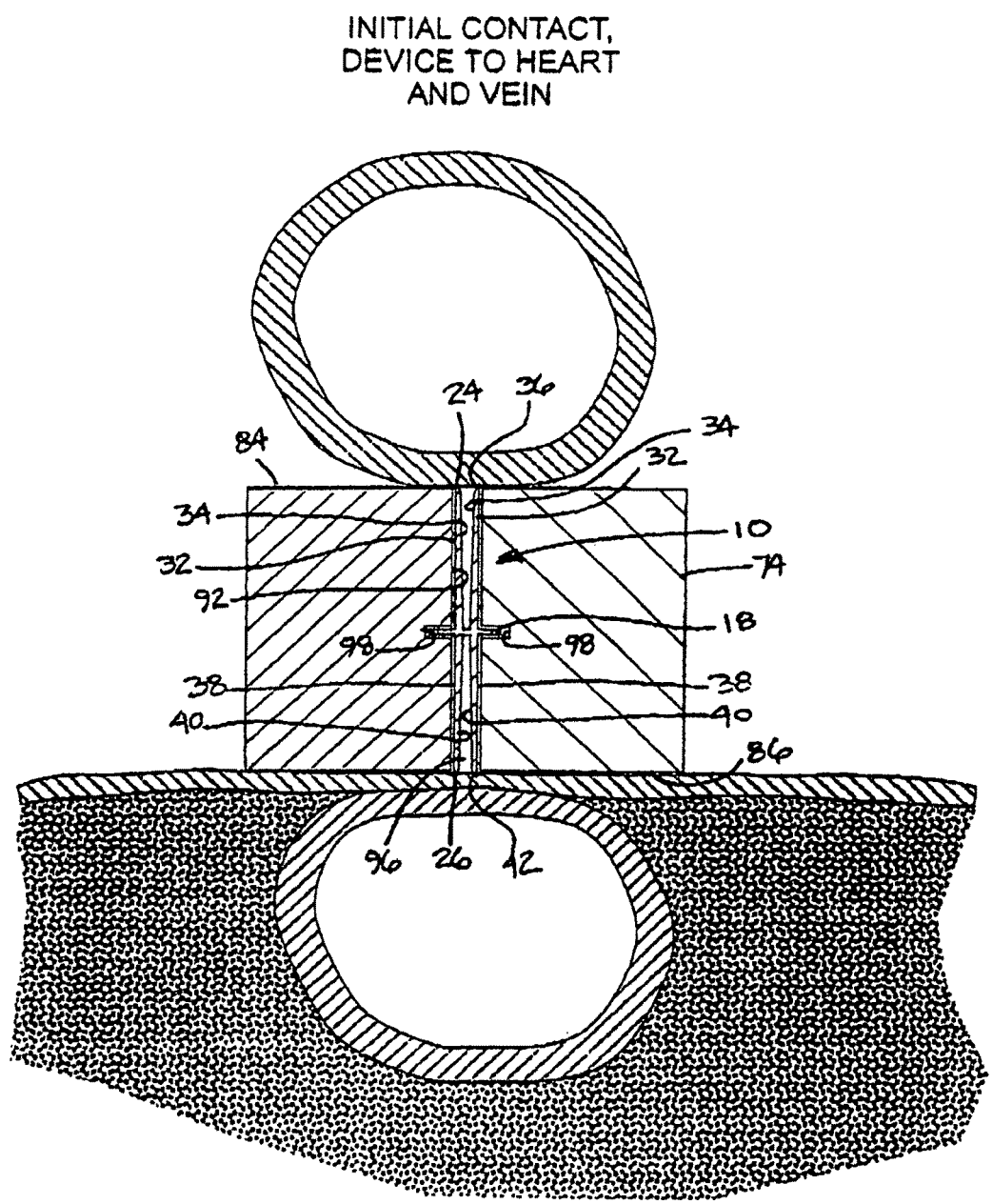
FIG. 21 is an enlarged partial cross-sectional view of the deployment apparatus overlying in a heart wall in abutting contact therewith with the fastener apparatus shown in its non-deployed configuration.

The first set of fingers 24 have an inner surface 32 and an outer surface 34 (FIG. 28) terminating at the free ends 28 that preferably define a point to facilitating piercing the tubular duct 12 and vessel 16, for example. As best shown in FIG. 21, when the first set of fingers 24 are in their biased and generally flattened configuration (as will be explained hereafter), the inner surfaces 32 face generally away from one another along the perpendicular axis 20 and the outer surfaces 34 face generally toward one another along the perpendicular axis 20. Desirably, the first set of fingers 24 each have a bevel 36, such that when in their biased configuration, the bevels 36 extend from each free end 32 generally toward the inner surfaces 32 and the perpendicular axis 20. The bevels 36 help to form a sharpened end 32 to allow the end 32 to more easily penetrate the tissue of a vessel.

The second set of fingers 26 have an inner surface 38 and an outer surface 40 terminating at the free ends 30 that preferably define a point to facilitating piercing the tubular duct 12 and vessel 16, for example. When the second set of fingers 26 are in their biased configuration as shown in FIG. 21, he inner surfaces 38 face generally away from each other along the perpendicular axis 20 and the outer surfaces 40 face generally toward each other along the perpendicular axis 20 and the inner surfaces 38 face generally away from the perpendicular axis 20. Desirably, the second set of fingers 26 each have a bevel 42 extending from each free end 30 generally toward the inner surfaces 38 and the perpendicular axis 20. The bevels 42 help to form a sharpened end 30 to allow the end 30 to more easily penetrate the tissue of a vessel.

The first and second sets of fingers 24, 26 are generally constructed in a symmetrical relation to each other such that they are axially aligned with one another about the circumference of the annulus 18, though they could be staggered relative to one another, if desired in the intended application. The fingers 24, 26 are constructed of a resiliently springy material having a shape memory so that they automatically return toward their unbiased, generally arcuate or hook shaped configuration when the force displacing or extending the fingers 24, 26 to their biased position (as for example as shown in FIG. 21) is removed. Desirably, shape memory alloys are used in constructing the fastener 10, thereby giving the first and second sets of fingers 24, 26 their resiliently springy properties. Some exemplary materials include, without limitation, nitinol, MP35N, tantalum, tungsten, platinum, 304 stainless steel, and other stainless steels, as desired for the intended application. While those materials listed are generally consider the preferred materials for the fingers 24, 26, any material that has a shape memory and that is biocompatible may be used including, without limitation, plastics and ceramics.

The fastener 10 is desirably fabricated from a thin, flat sheet of material, for example, from one of the materials listed above or having the functional characteristics mentioned above. The thickness of the material used to construct the fastener 10 depends greatly on the physical properties of the material including the elasticity of the material. As shown in FIG. 2, in fastener 10's initial construction, the first and second sets of finger 24, 26 extend radially inwardly from an annulus 18. Thereafter, fingers 24, 26 are heat formed into their final shape (i.e., the shape having the bias to form the arcuate "C" shape configuration described above), as is discussed hereafter in more detail.

Desirably, when the fingers 24, 26 are in their biased, first positions, the material chosen remains in an elastic state of deformation, thereby biasing the fingers 24, 26 to return to their second, relaxed positions. Using 304 stainless steel, one of the materials listed above, a thickness of about 0.0001"-0.0150" is generally preferred, though it should be understood that the thickness may vary according to the material used as will be well understood in the art.

As best shown in FIG. 2, the first step in the construction of the fastener 10 is to produce a generally flat annular pattern (generally referred to by the reference number 10) from a sheet of material, wherein the pattern has the first and second sets of fingers 24, 26 extending radially inwardly toward one another. Desirably, the pattern has diametrically opposite loops 21 extending radially outwardly from the annulus 18. The loops 21 act at least in part as spring joints to facilitate returning the apparatus 10 to its unbiased form upon deployment of the fastener 10 as will be described hereafter. The method of manufacture of the fastener 10 may incorporate a variety of construction methods, for example and without limitation, photo-chemical etching, laser cutting, die punching, electric discharge machining (EDM), and other methods of construction, as desired and as well understood by those skilled in the art. It should be understood that the first and second sets of fingers 24, 26 may be constructed having different lengths from one another.

To facilitate bonding between tissue and the fastener 10 as part of the healing process after the fastener 10 is placed, both sides of the flat annual pattern, particularly the inner surfaces 32, 38 and the outer surfaces 34, 40 are preferably provided with a surface texture or roughed generally having a surface finish of about 30-60 RMS using a process such as chemical etching, or mead-blasting, for example. By creating a roughed surface, the tissue is better able to bond to the fastener 10. Alternately, the fastener 10 may be coated either at the first stage of construction or later with a material to facilitate or strengthen tissue growth or minimize infections or a combination of these.

Figure 4:
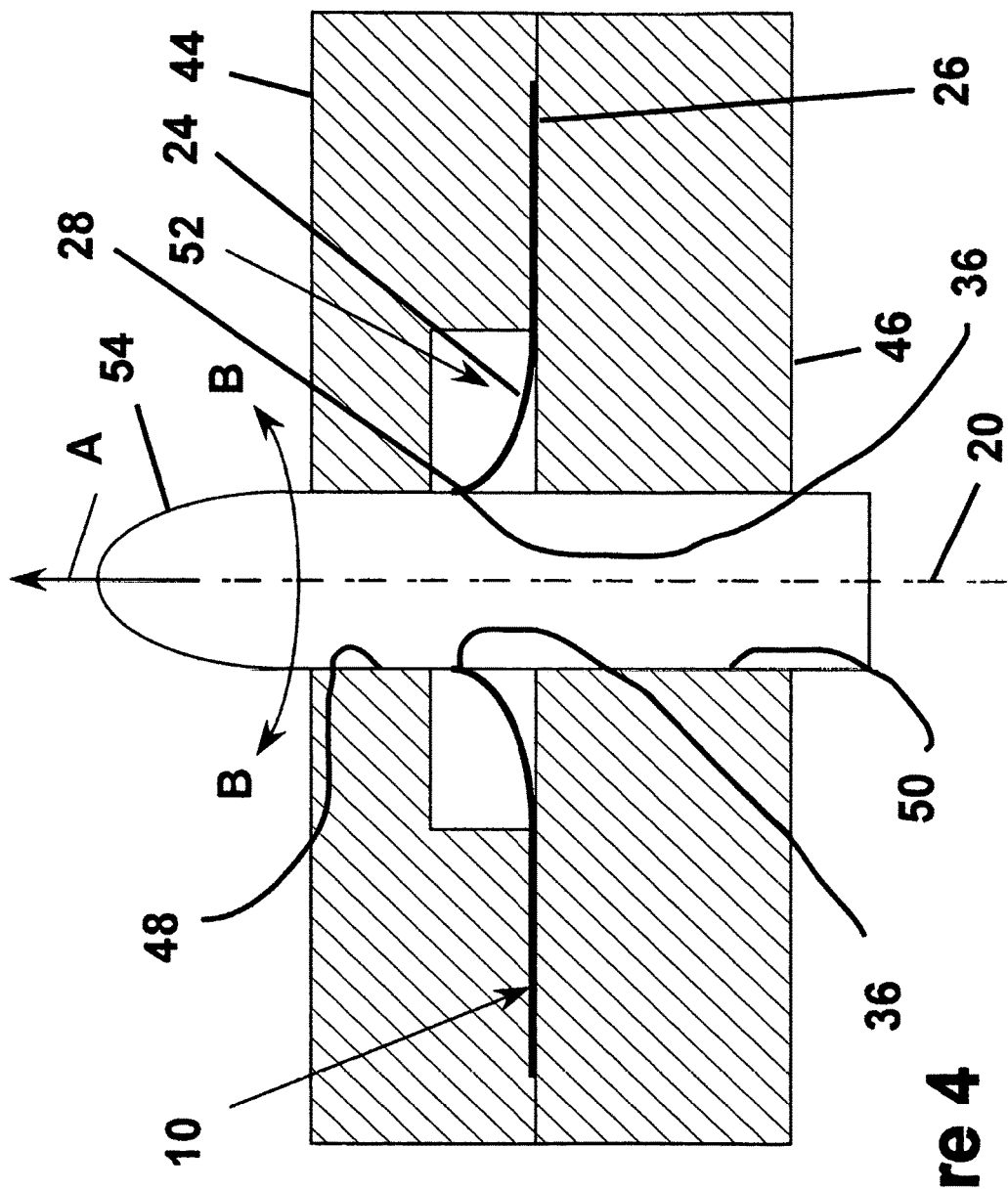
FIG. 4 is a cross-sectional view of the apparatus maintained between a pair of plates with a sharpening tool forming bevels on a first set of fingers of the apparatus.

As shown in FIG. 4, desirably, while the fastener 10 is in its initially constructed flat configuration, the bevels 36 are formed on the first set of fingers 24. While forming the bevels 36 on the first set of fingers 24, the flat annual pattern is placed between a pair of generally flat dies or plates 44, 46. Each plate 44, 46 has a through hole 48, 50, respectively, sized to allow the first set of fingers 24 to extend radially inwardly into the through holes 48, 50 upon concentrically aligning the through holes 48, 50 and the first set of fingers 24 with one another along the axis 20. The plate 44 has a counter bore 52 to allow the first set of fingers 24 to deflect during the formation of the bevels 36.

In forming the bevels 36 on the first set of fingers 24, the fastener 10 is maintained between the plates 44, 46 so that a sharpening tool, for example and without limitation, a honing rod 54, can be passed in one direction, represented by arrow A, through the through holes 48, 50 of the plates 44, 46 to engage the free ends 28 of the first set of fingers 24. Accordingly, as the honing rod 54 engages the first set of fingers 24, the fingers deflect generally in the direction of arrow A, into the counter bore 52. As such, material is removed from the first set of fingers 24 to form the bevels 36. It should be recognized that the honing rod 54, in addition to being passed axially through the through holes 48, 50 of the plates 44, 46, can be rotated about the axis 20 in the direction of arrows B to facilitate forming a uniform bevel 36 on each of the first set of fingers 24.

Figure 5:
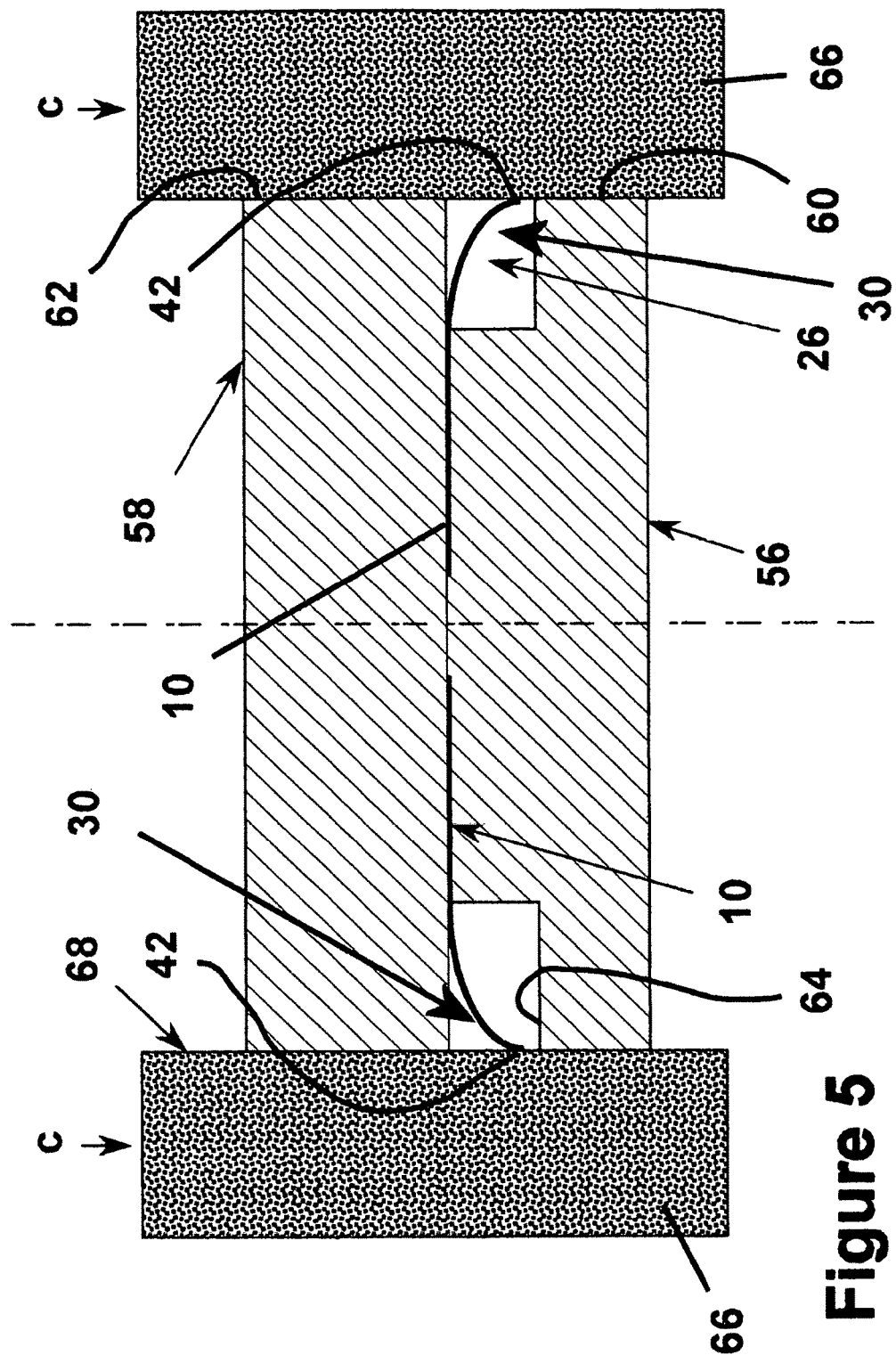
FIG. 5 is a cross-sectional view of the apparatus maintained between another pair of plates with a sharpening tool forming bevels on a second set of fingers of the apparatus.
Figure 9:
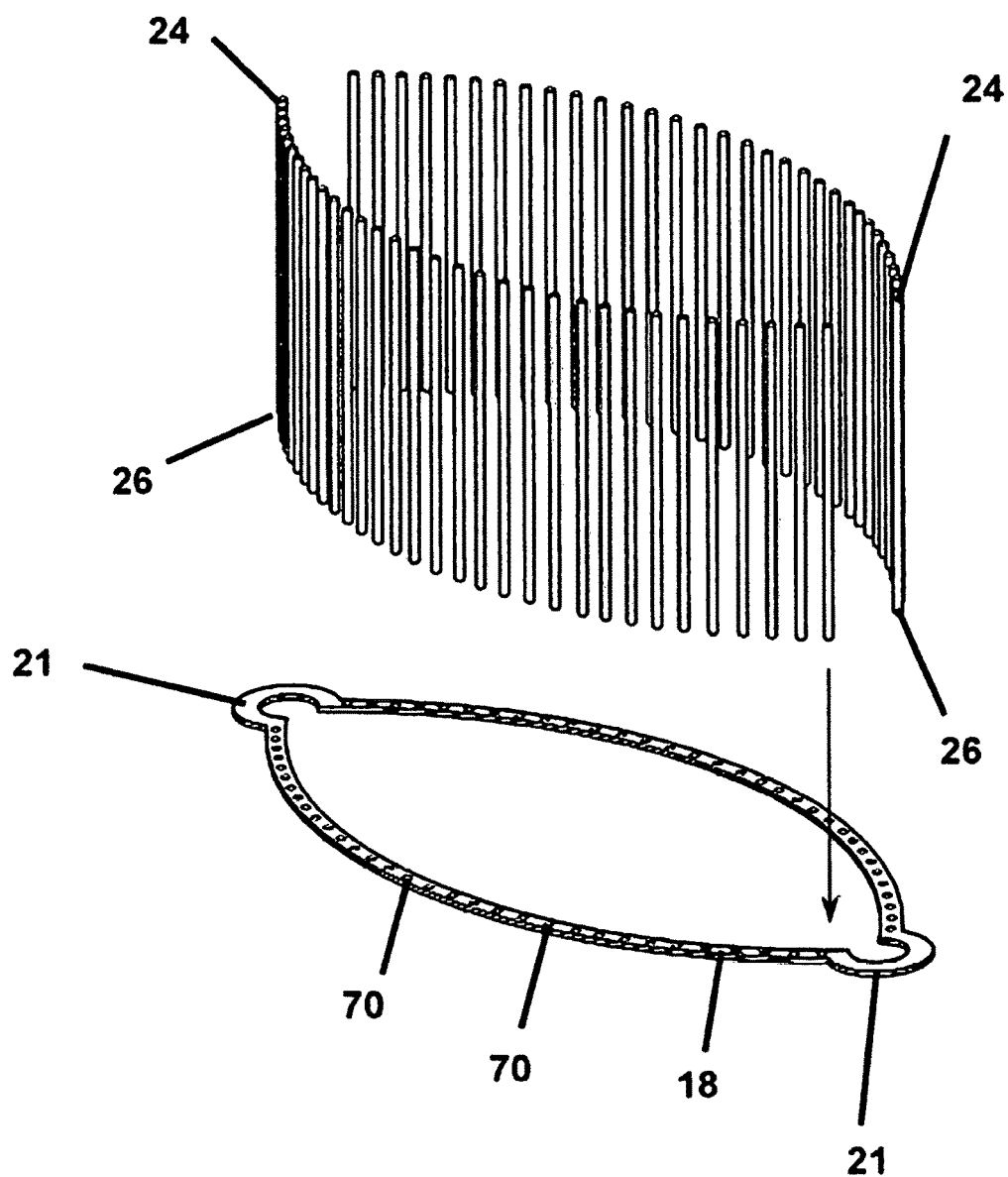
FIG. 9 is an exploded perspective view of the annulus of FIG. 7 with a plurality of fingers arranged to be received in a corresponding number of openings in the annulus.

As shown in FIG. 5, desirably, while the fastener 10 is in its initially constructed flat configuration, the bevels 42 are formed on the second set of fingers 26. While forming the bevels 42 on the second set of fingers 26, the flat annual pattern is placed between a pair of generally flat dies or plates 56, 58. Each plate 56, 58 has an outer diameter 60, 62, respectively, sized to allow the second set of fingers 26 to extend radially outwardly therefrom upon concentrically aligning the outer diameters 60, 62 and the second set of fingers 26 with one another along the axis 20, with the fastener 10 maintained between the plates 56, 58. The plate 56 has a recessed surface 64 to allow the second set of fingers 26 to deflect during the formation of the bevels 42.

In forming the bevels 42 on the second set of fingers 26, the fastener 10 is maintained between the plates 56, 58 so that a sharpening tool, for example and without limitation, a honing cylinder 66, can be passed in one direction, represented by arrows C, generally in the same direction as arrow A in which the honing rod 54 is passed, to engage the free ends 30 of the second set of fingers 26. The honing cylinder 66 has a bore 68 greater in diameter than the outer diameters 60, 62 of the plates 56, 58 and less than the outer diameter of the second set of fingers 26. Accordingly, as the honing cylinder 66 passes over the second set of fingers 26, the bore 68 engages the free ends 30 of the second set of fingers 26 to deflect the fingers 26 generally in the direction of arrow C, toward the recessed surface 64. As such, material is removed from the second set of fingers 26 and the bevels 42 are formed.

The flat annular pattern, as shown in FIG. 2, is then elastically deformed to provide the finished, unbiased shaped of the fastener 10, as best shown in FIGS. 1 and 3 by preferably bending or deforming alternate fingers upwardly and downwardly, respectively, to form the first and second sets of fingers 24, 26, and to form the radially outwardly extending flange 19. The deformed pattern is maintained in the desired finish shape by subjecting the elastically deformed pattern to a controlled heat treatment process. During the heat treatment process, the deformed pattern is raised to the critical temperature of the material, for example, about 932.degree. F. for nitinol, between about 800-1200.degree. F. for MP35N, and is then quenched, preferably in water, to retain the pattern in conformity with the outer surfaces of the dies. Upon finishing the heat treatment process, the first set of fingers 24 are shaped to their unbiased, generally arcuate configuration extending at least partially generally radially outwardly from the perpendicular axis 20, while the second set of fingers 26 are shaped to their unbiased, generally arcuate configuration extending at least partially generally radially outwardly from the perpendicular axis 20.

Alternatively, as shown in FIGS. 6-8, the fastener 10 may be fabricated from separate pieces of selected material, such as from the aforementioned materials, wherein the annulus 18 is fabricated separately from the fingers 24, 26. A plurality of through openings 70 are formed about the circumference of the annulus 18 at predetermined and preferably equally spaced locations from one another. Through openings 70 may be formed by any means well known in the art including, but not limited to, micro-drilling, etching or laser-drilling.

The annulus 18 is then preferably heat formed to its intended finish shape (FIG. 7), whereupon the one piece fingers 24, 26 are inserted into the through openings 70 a predetermined distance, and preferably to their midpoint. The fingers 24, 26 are preferably fixed in the openings by way of a weld joint such as is well understood by those skilled in the art.

Upon forming the fastener 10 to its finished configuration, the fastener 10 is preferably subjected to a passivating process to remove any impurities from the surfaces of the fastener 10. The passivation may be achieved by electropolishing, chemical passivation, or a hybrid technique known as selective abstraction passivation. The electropolishing passivation process utilizes a reducing acid environment in conjunction with a source of DC power. The electropolishing process removes impurities from the surfaces of the fastener 10 to a depth of about 20-30 angstroms, depending on the exposure time of the fastener 10 to the reducing acid environment and DC power. The chemical passivation process can be performed in a variety of manners, for example, pickling, wherein the fastener 10 is immersed in a solution of hydrofluoric acid (HF) and nitric acid (HNO3) for a period of time; chelant passivation (citric acid), and selective abstraction, wherein a specifically formulated abstraction chemistry is used in conjunction with electrolysis. The selective abstraction technique removes only the readily soluble passive film contaminants such as iron, nickel, aluminum (grinding residue), and the like. Upon passivating the surfaces of the fastener material, desirably the fastener 10 is cleaned utilizing a plasma cleaning process.

The plasma cleaning process removes all foreign materials remaining on the surfaces of the fastener material. Some of the plasma cleaning mechanisms that may be used includes, for example, induction coupled barrel reactors and capacitance coupled parallel plate reactors.

Upon cleaning the surfaces of the fastener 10, preferably the surfaces are at least partially coated with a bio-adhesive material to facilitate forming a cohesive bond between the fastener 10, the tubular duct 12 and the vessel 16. The bio-adhesive materials may include by-products of the patient's own blood, for example, platelet gel formed from the patient's blood. Otherwise, biocompatible adhesives including calcium, for example and without limitation, may be used. These same bio-adhesives may also be introduced while attaching the fastener 10 to the tubular duct 12 and the vessel 16, as discussed in more detail hereafter. As shown generally in FIGS. 10A-10G, upon coating the fastener 10 with the bio-adhesive, the fastener 10 is generally ready for deployment by an apparatus, referred to hereafter as a deployment tool 72.

Figures 10A, 10B, 10C, 10D, 10E, 10F, 10G:
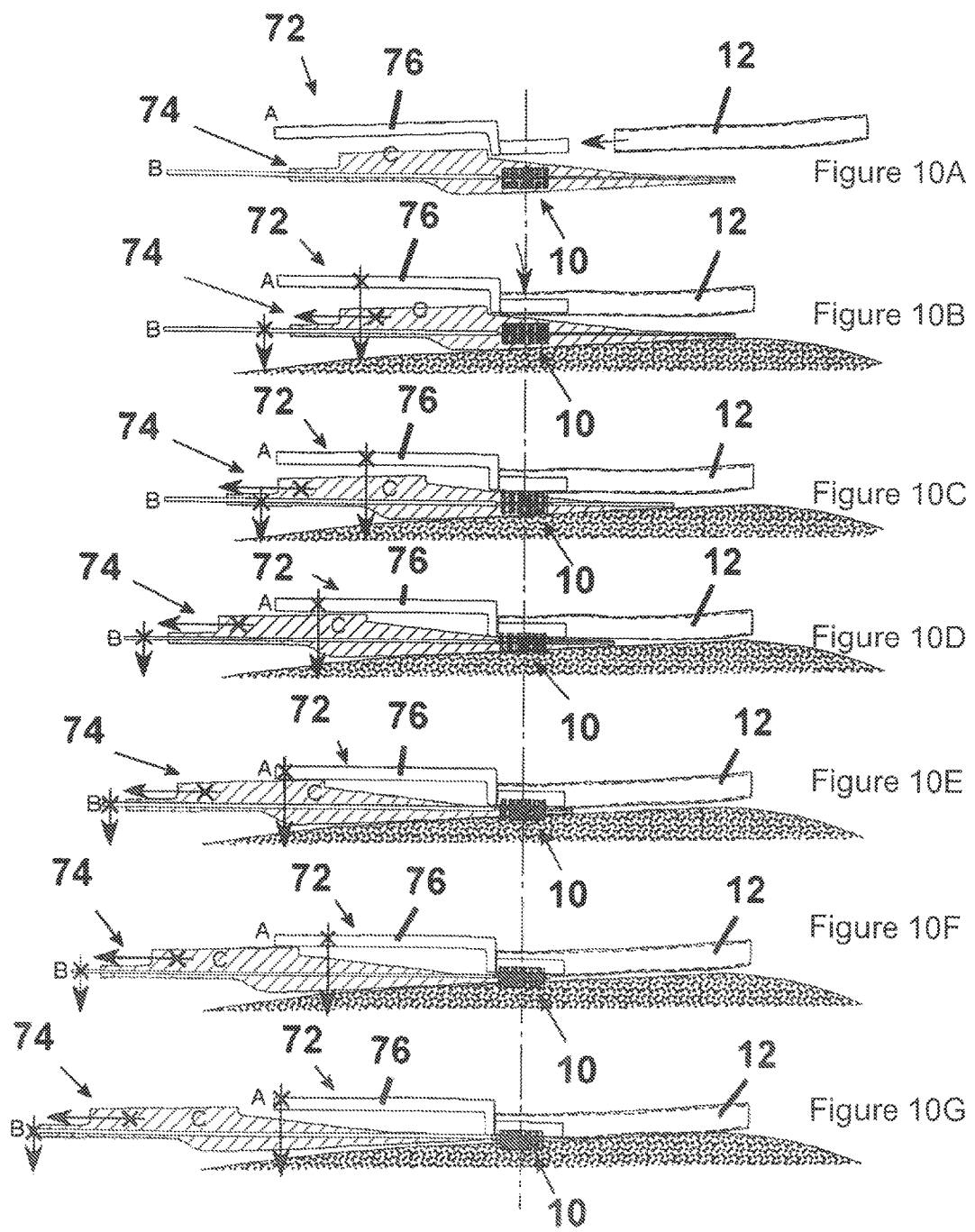
FIGS. 10A-10G are schematic side views of a deployment apparatus shown joining a tubular duct to a vessel.
Figure 12:
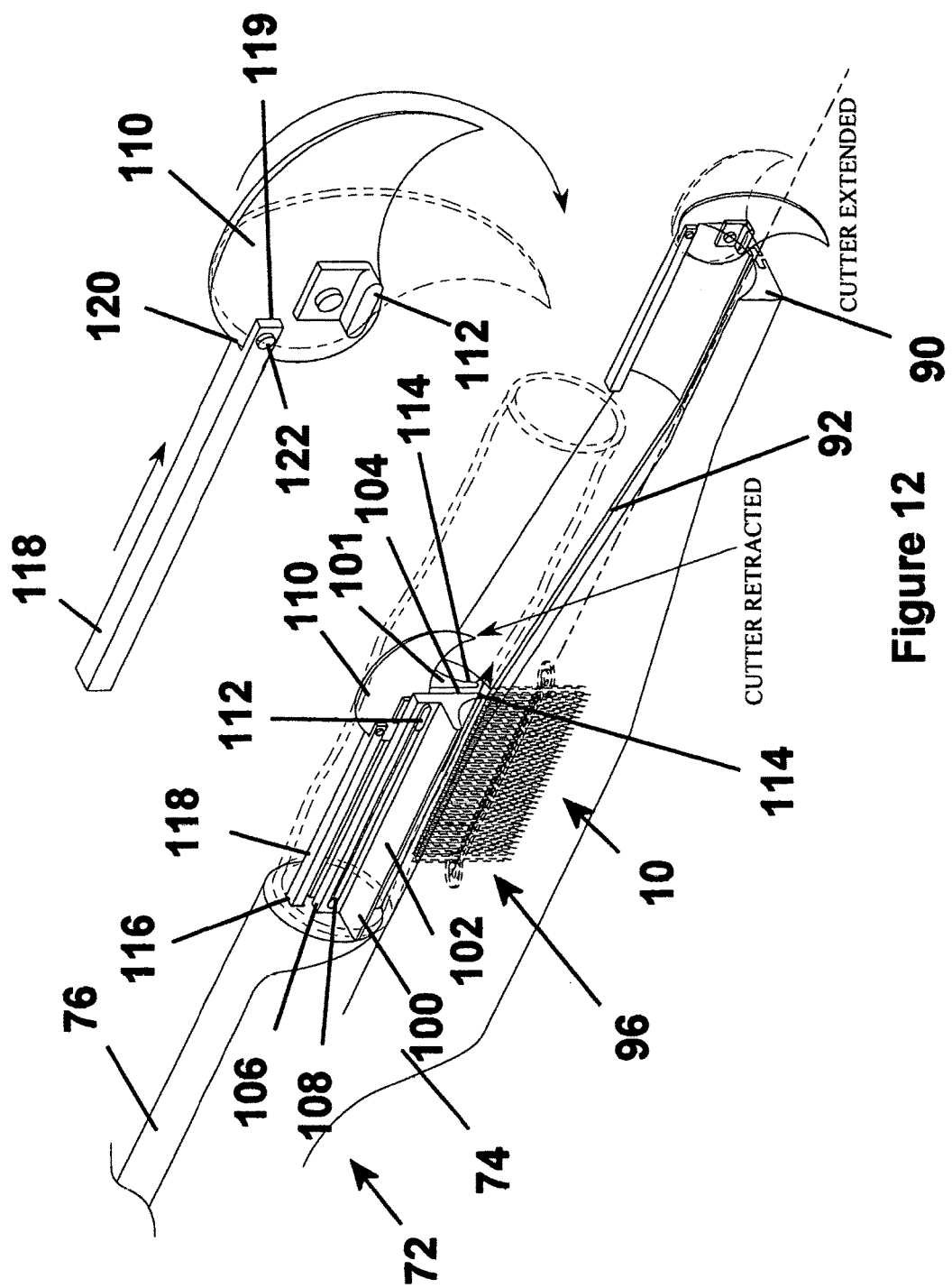
FIG. 12 is a perspective view of the deployment apparatus of FIG. 11 showing the fastener apparatus loaded therein and a receptacle of the deployment apparatus with a cutter shown in retracted and extended positions.
Figure 13:
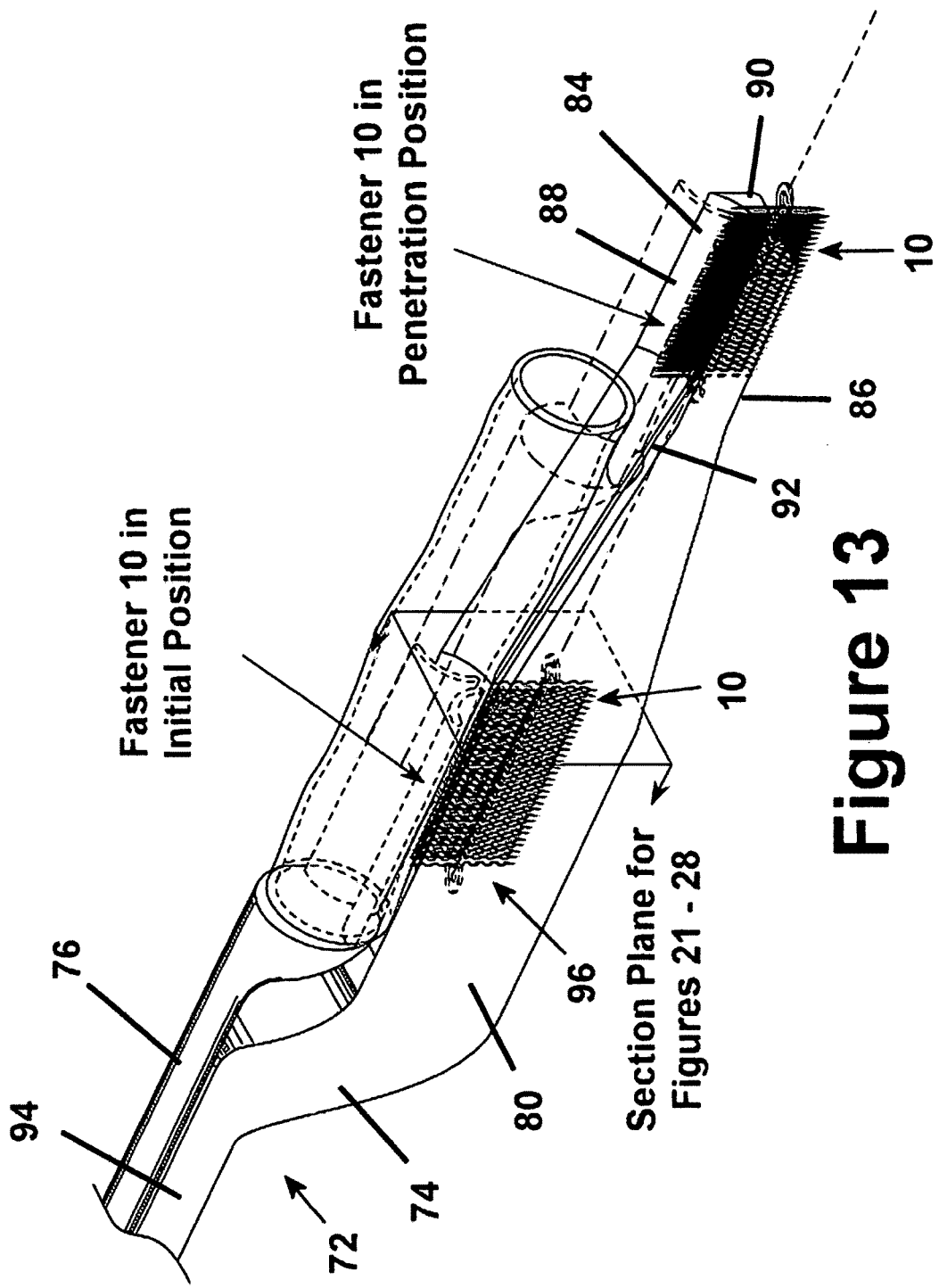
FIG. 13 is a view similar to FIG. 12 with the cutter removed and showing the fastener apparatus in an initially loaded position and a deployed position.

As shown in FIG. 10, the deployment tool 72 has a main body 74 with a luminary guide, hereafter referred to as a guide member 76, received on the main body 74 for slidable relative movement therealong between a retracted loading position (FIG. 10A) and an extended deploying position (FIG. 10G). As shown in FIGS. 11-13, to facilitate the slidable movement of the guide member 76, the body 74 preferably has a lateral slot 78 within one and preferably opposite sidewalls 80 of the body 74 for receipt of guide fingers 82 depending from the guide member 76. The body 74 has upper and lower walls 84, 86 with inclined surfaces 88 preferably having concave surfaces converging toward each other adjacent an end 90 of the body 74. A longitudinal channel 92 extends through the upper and lower walls 84, 86 from the end 90 of the body 74 toward a handle 94 of the body 74. The channel 92 has sidewalls that define a fastener cavity 96 sized to receive and maintain the fastener 10 in its biased and generally flattened position between the sidewalls by engaging the fingers 24, 26 of the fastener 10 until a user is ready to deploy the fastener 10 into the selected tissues, as shown in part in FIG. 12. It should be understood that though FIG. 12 shows the fingers 24, 26 still in their biased position for demonstration of the slidable movement of the fastener apparatus 10, they actually would take on their nonbiased curved configuration in use. A pair of recesses 98 (FIGS. 21-24) extend laterally outwardly from the channel 92, wherein the recesses 98 are sized to receive the annulus 18 of the fastener 10 to facilitate guided slidable movement of the fastener 10 through the channel 92. The channel 92 is also sized to allow a portion of the guide member 76 to slide therethrough as the main body 74 of the deployment apparatus 72 is moved axially relative to the guide member 76.

As shown in FIG. 12, the guide member 76 has an axially extending receptacle 100 sized to receive the tubular duct 12 thereon. The receptacle 100 has a pair of bodies 101, 102 spaced laterally from one another to define a cutter channel 104. Each body 101, 102 preferably has upwardly extending flanges 106 with cutter slots 108 extending axially along each flange 106. The slots 108 carry a cutter 110 via tabs 112 extending laterally outwardly from the cutter 110 for slidable movement within the slots 108. Preferably, each body 101, 102 has a lower concave surface 114 flaring from a bottom of the bodies 101, 102 laterally outwardly from one another to provide partially guided support for the fastener apparatus 10 as it is being deployed.

Figure 25:
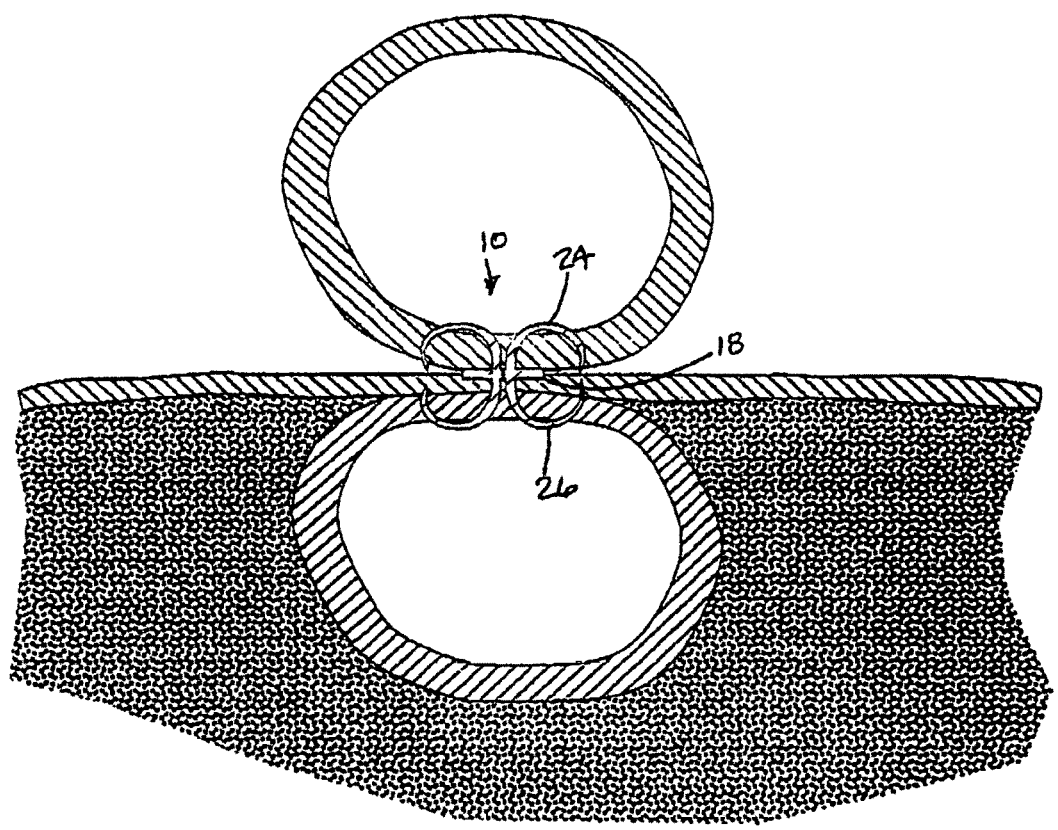
FIG. 25 is a view similar to FIG. 24 with fastener apparatus shown in a more advanced state of deployment.

The function of cutter 110, as will be explained in detail hereafter, is to cut tissue. Specifically, the function of cutter 110 is to cut the tissue of the wall 11 of the tubular duct 12 and the wall 14 of a vessel 16 after the fastener 10 is deployed in the tissue of the tubular duct 12 and vessel 16 as shown in FIG. 25. Consequently, cutter 110 must have a sharp edge that may cut the tissue of the tubular duct 12 and vessel 16. In one embodiment of the fastener 10, the cutter 110 may take the form of a small surgical blade. In another embodiment of the fastener 10 the cutter 110 may take the form of a sharpened surgical wire. Other forms for cutter 110 will occur to those skilled in the art that meet the functional requirements of cutter 110 as explained herein.

The guide member 76 has a housing 116 sized for reciprocating movement of an actuator rod 118. The rod 118 has one end 119 preferably having a notch 120 arranged for attachment to the cutter 110 via a pin 122 to provide pivotal movement of the cutter 110 relative to the rod 118, and another end arranged for operable attachment to an actuator trigger mechanism. Accordingly, when the trigger mechanism is actuated, such as by being moved from a first retracted position to a second depressed position, the actuator rod 118 slides within the housing 116 toward the trigger, thereby causing the blade 110 to pivot to a cutting position. In addition, to the pivotal movement of the cutter 110, the cutter 110 is caused to slide within the cutter channel 104 from a free end of the receptacle 100 toward the handle or trigger during a cutting procedure by pulling on the trigger. As such, the cutter 110 moves from an extended initial position to a retracted final position upon making an incision.

Figure 14:
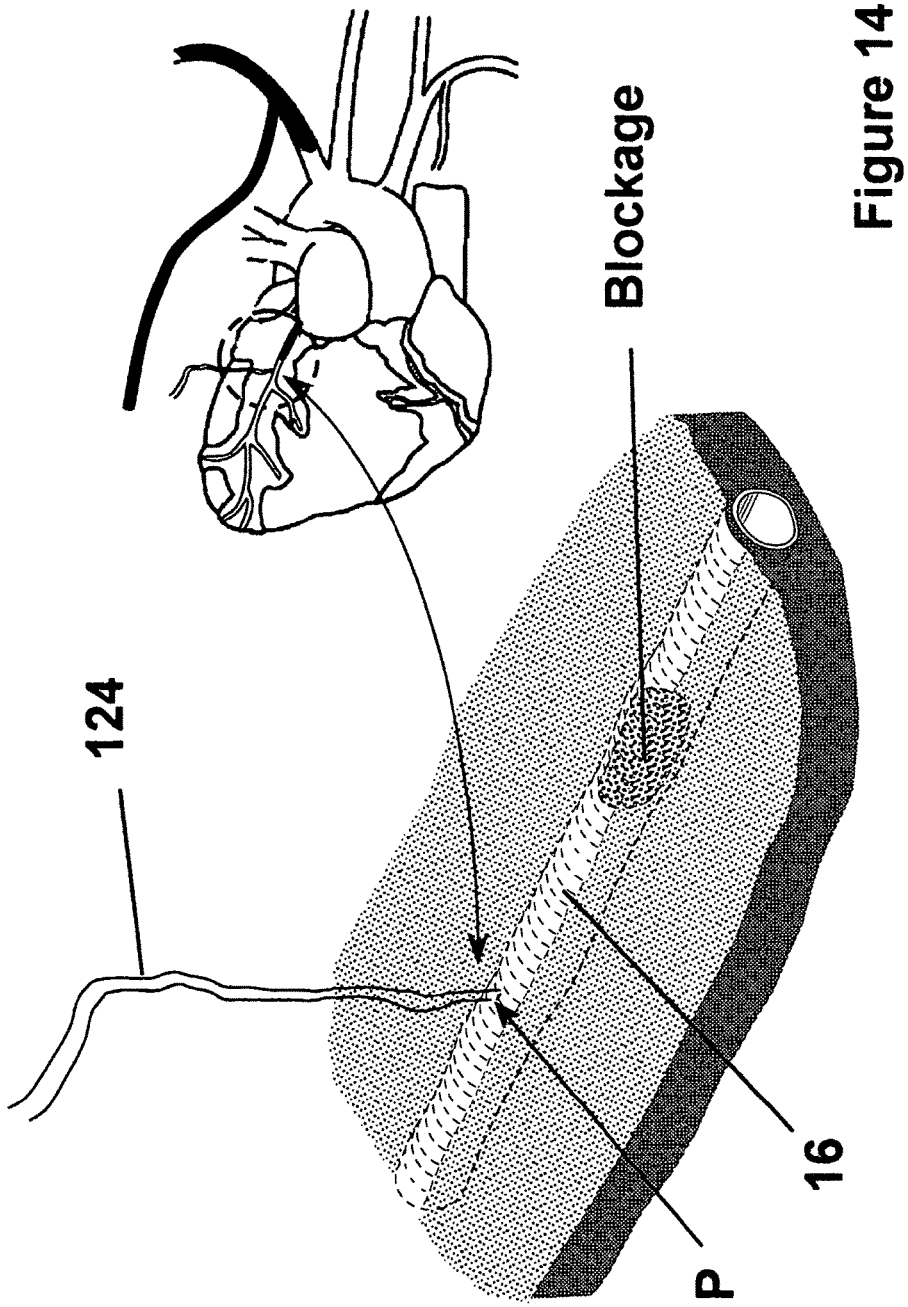
FIG. 14 is an enlarged perspective view of a portion of a heart showing a point of attachment of a tagging suture to a tubular duct within the heart.
Figure 15:
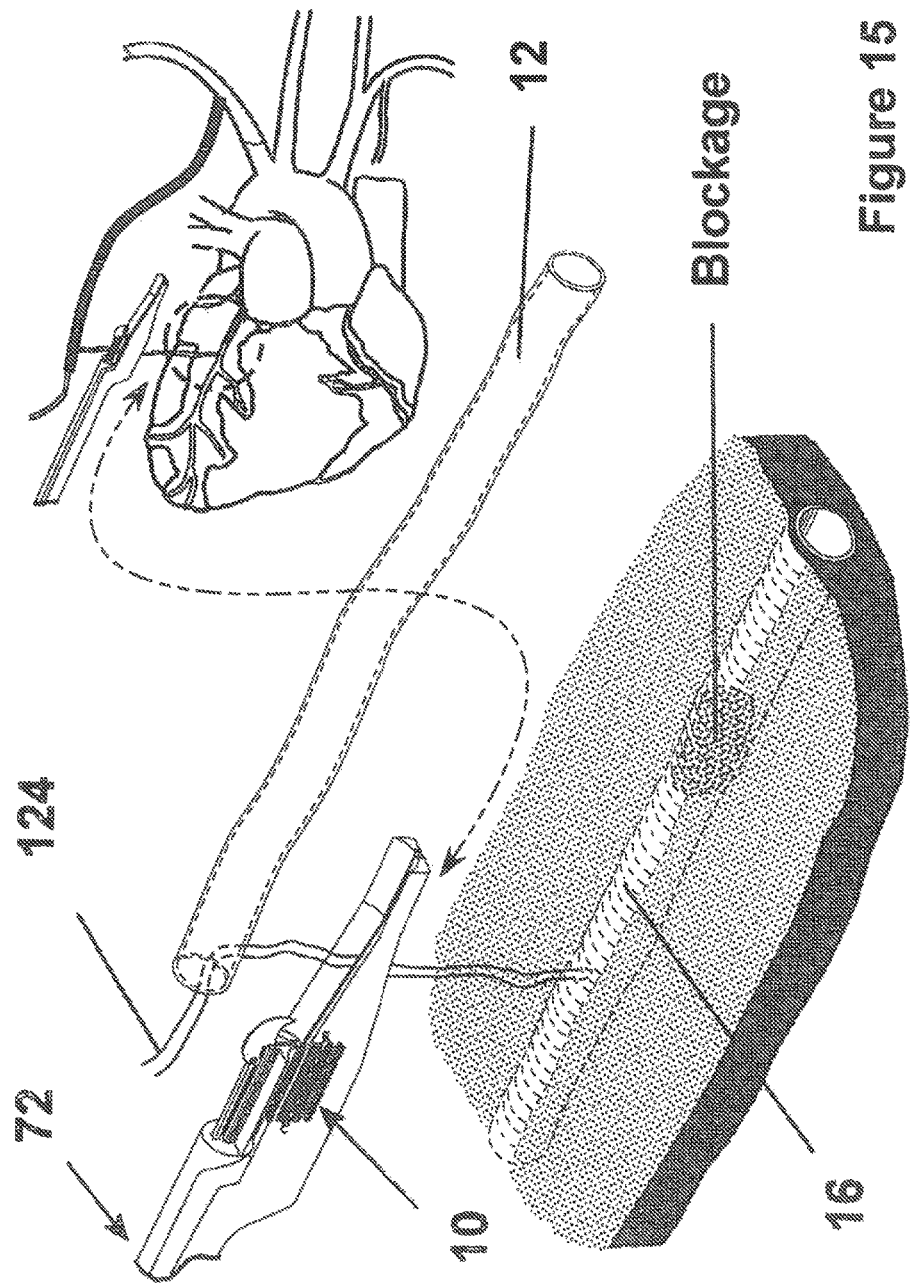
FIG. 15 is a view similar to FIG. 14 showing the tagging suture received through the deployment apparatus and attached to a tubular duct graft.

In deployment, as shown in FIG. 14, the surgeon can facilitate locating the fastener apparatus by tagging a point (P) of attachment on the vessel 16 with a suture 124. As shown in FIG. 15, at least one of the ends and shown here as both ends of the suture 124 are fed through at least one of the loops 21 in the fastener apparatus 10 and through the axial channel 92 in the main body 74 of the deployment apparatus 72. The suture ends are then preferably stitched through the tubular graft 12 adjacent its end.

Figure 16:
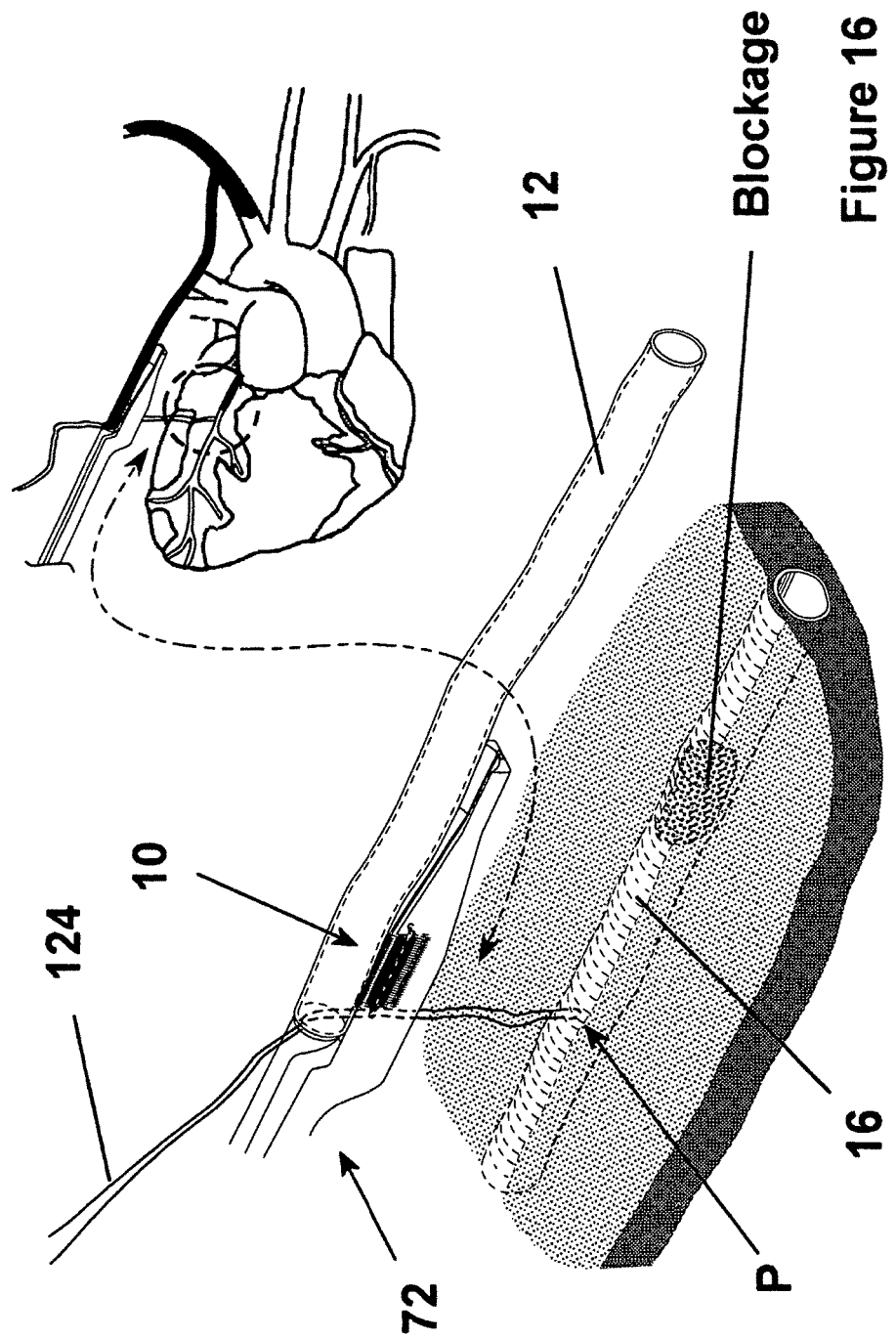
FIG. 16 is a view similar to FIG. 15 showing the graft of FIG. 15 received on the receptacle of the deployment apparatus.
Figure 17:
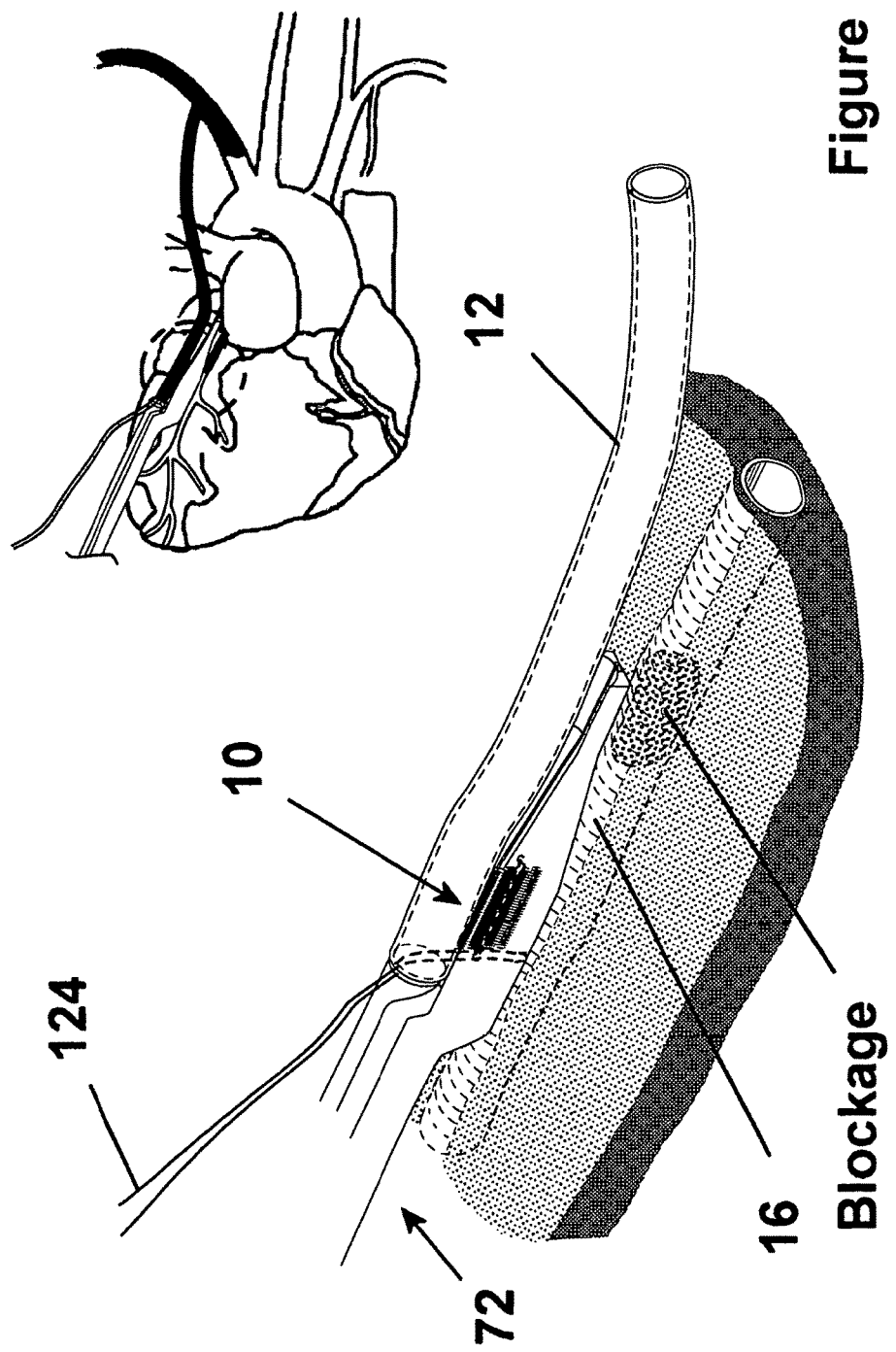
FIG. 17 is a view similar to FIG. 16 showing the deployment apparatus disposed in position to initiate attachment of the graft to the tubular duct underlying the heart wall.
Figure 18:
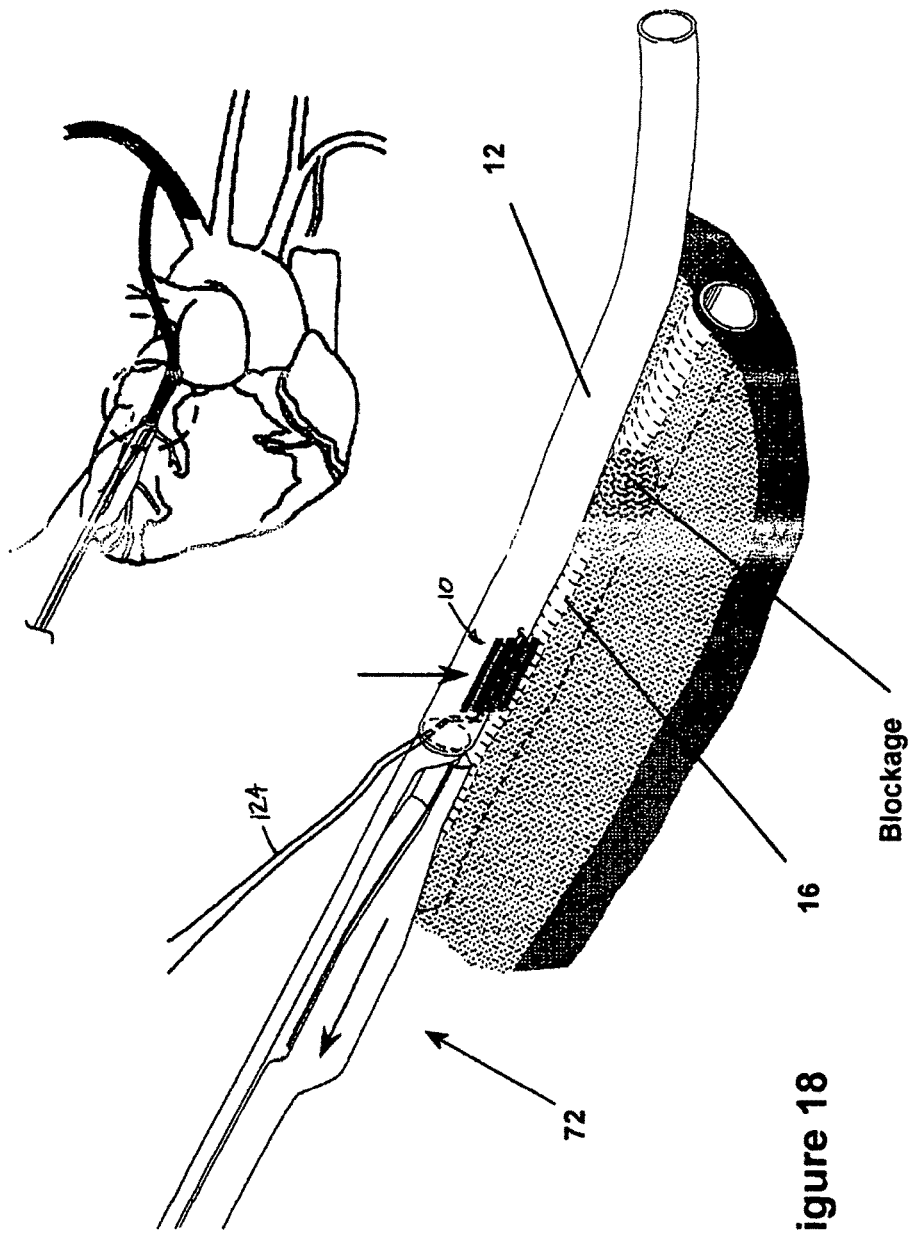
FIG. 18 is a view similar to FIG. 17 showing the fastener apparatus being deployed to form an anastomosis between the graft and the tubular duct underlying the heart wall.

As shown in FIG. 16, the graft 12 is then disposed on the receptacle 100 with the suture 124 being received in part between an end of the graft 12 and the deployment apparatus 72. As shown in FIGS. 17 and 21, the deployment apparatus 72, with graft thereon, is positioned on the vessel 16, as facilitated by the guided assistance provided by the tagged suture 124. Thereafter, the fastener apparatus 10 is deployed by preferably pulling the main body 74 to move the guide member 76 to its extended deployed position, as shown in FIGS. 18 and 22-25. It should be understood that though FIG. 18 shows the fingers 24, 26 still in their biased position for demonstration of the slidable movement of the fastener apparatus 10, they generally would take on their nonbiased curved configuration in use to attach themselves to the graft 12 and the underlying tissue vessel 16.

Figure 22:
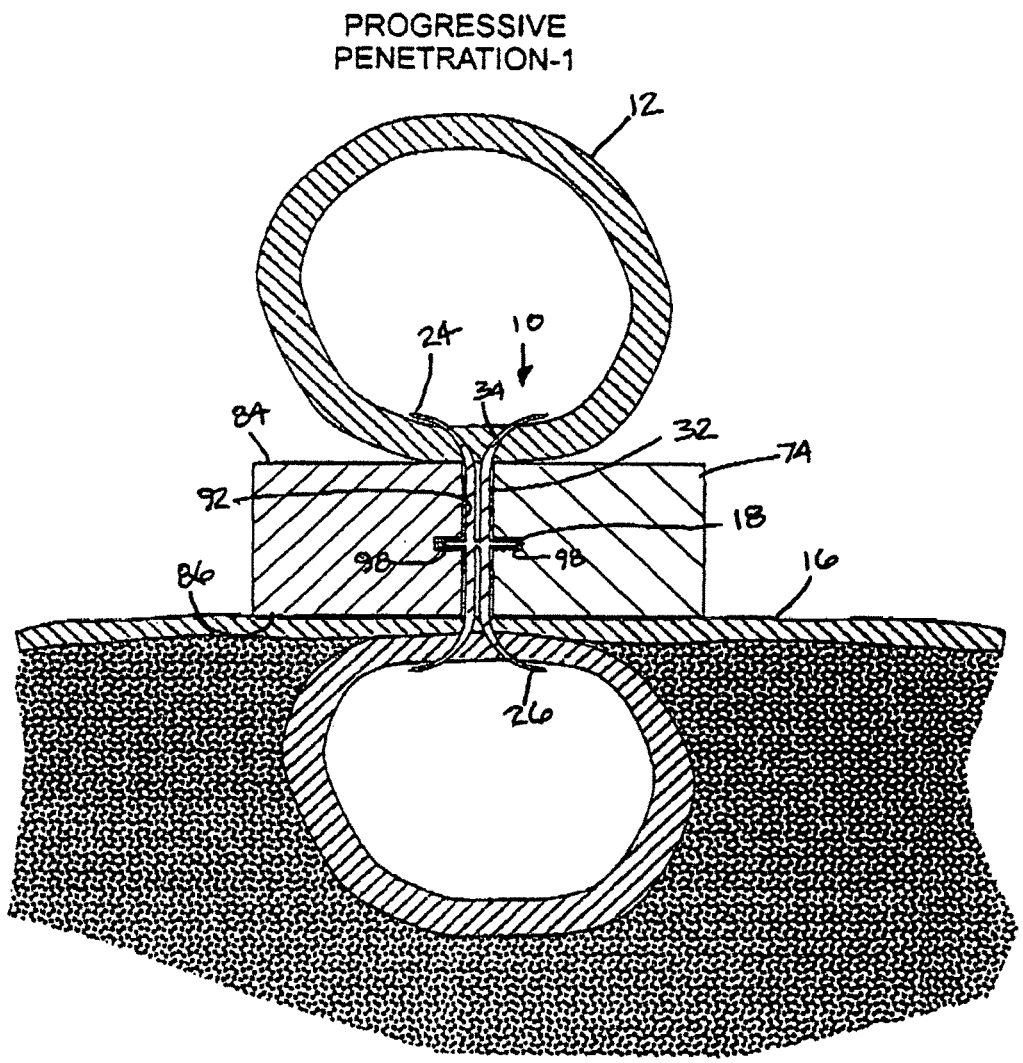
FIG. 22 is a view similar to FIG. 21 with the fastener apparatus shown in a partially deployed configuration.
Figure 23:
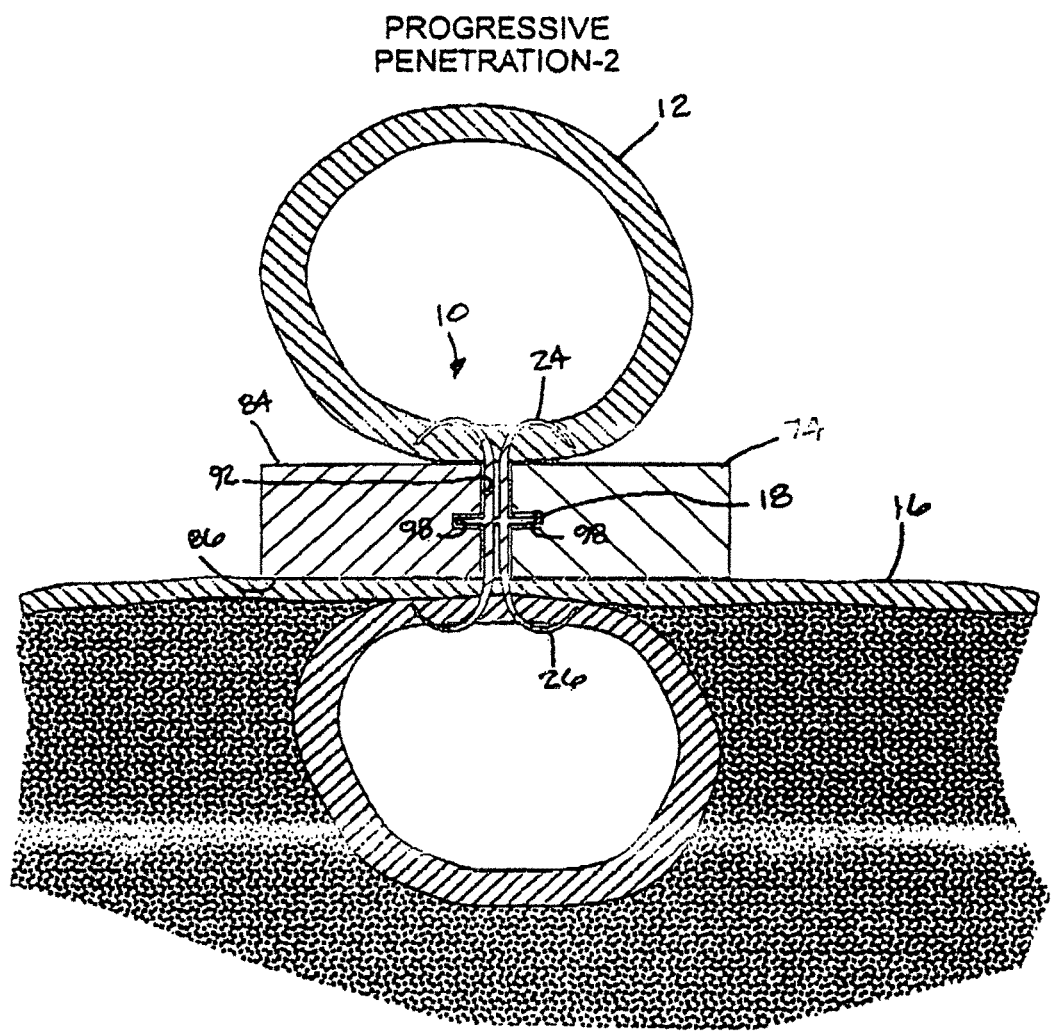
FIG. 23 is a view similar to FIG. 22 with the fastener apparatus shown in a more advanced state of deployment.
Figure 24:
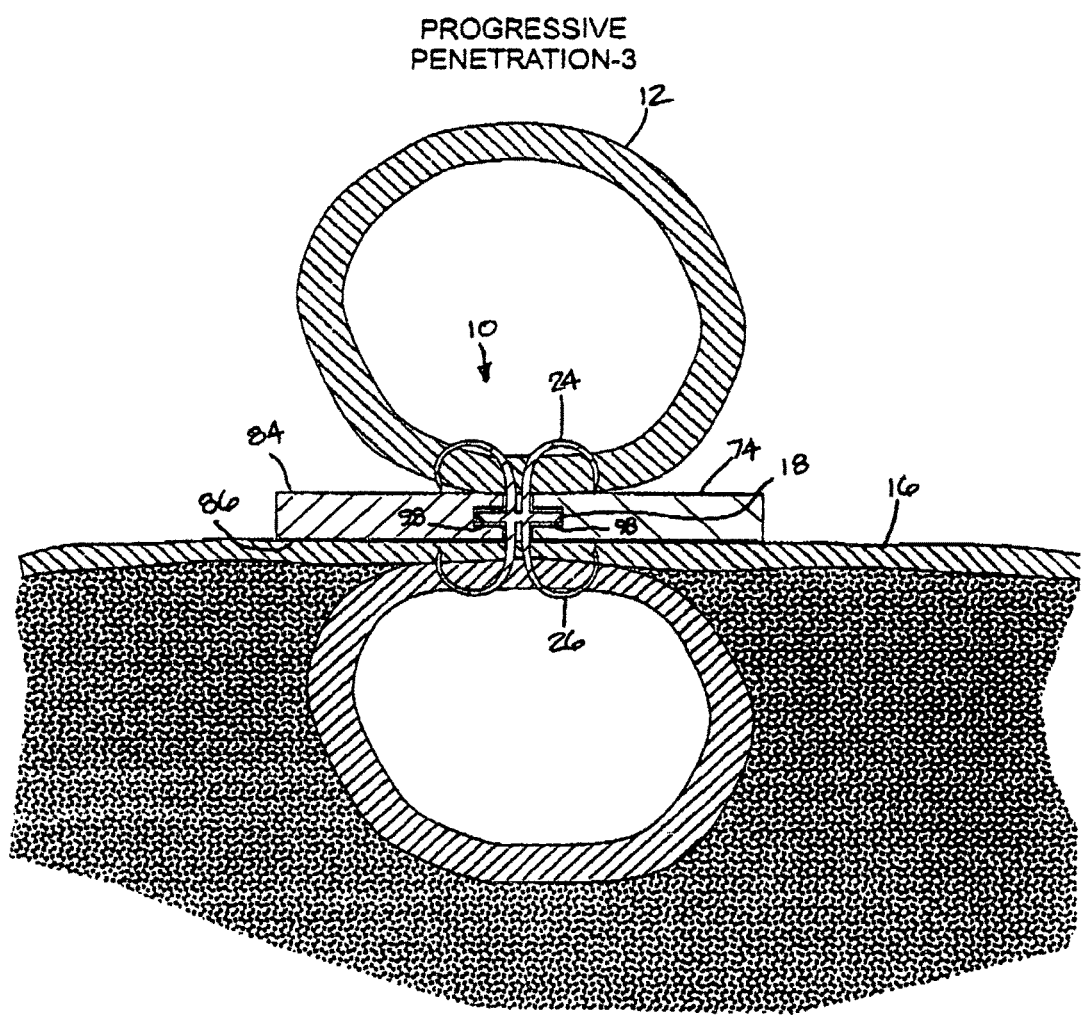
FIG. 24 is a view similar to FIG. 23 with fastener apparatus shown in a more advanced state of deployment.

In FIGS. 22-25, the fingers 24, 26 of the fastener apparatus 10 are shown in progressive states of movement as they take on their unbiased form and are deployed into the tissues being joined. The fingers 24, 26 begin to take their unbiased shape upon clearing the confines of the main body 74 of the deployment apparatus 72 as the main body 74 is pulled, and as the receptacle 100 and the graft 12 are slid downwardly along the upper wall 84 of the main body 74 (FIG. 22). At the same time, the underlying tissue vessel 16 slides along the lower wall 86, thus allowing the lower fingers 26 to penetrate the underlying tissue vessel 16 at the same time and rate as the upper fingers 24 penetrate the graft 12. In FIG. 23, the fingers 24, 26 are shown in a partially curled state where they begin to turn back generally toward one another, thereby preferably imparting a bias to pull the graft 12 and the underlying tissue vessel 16 toward one another.

Figure 19:
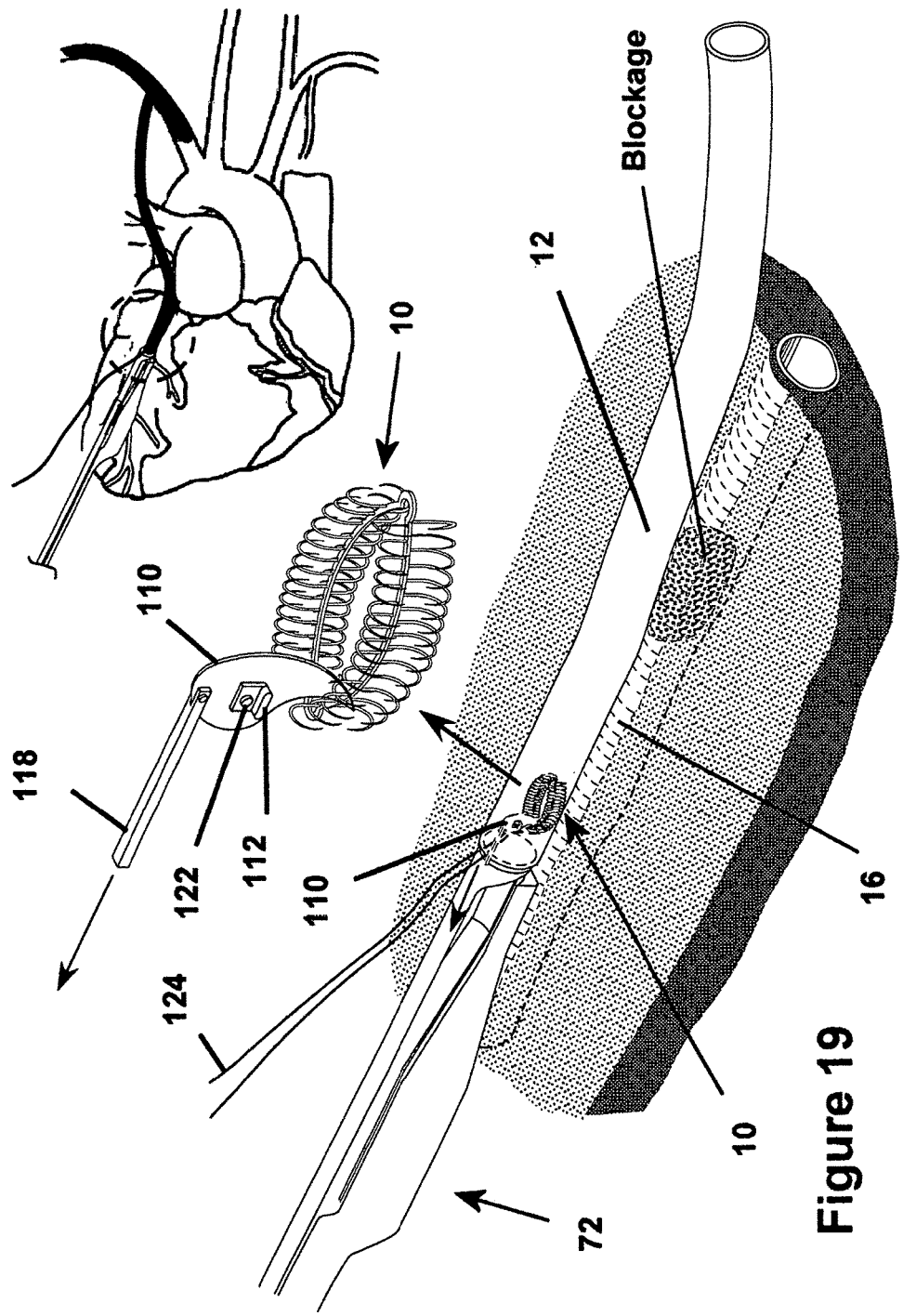
FIG. 19 is a view similar to FIG. 18 showing the cutter being moved from its extended position toward its retracted position to form and opening between the graft and the tubular duct within the heart.
Figure 20:
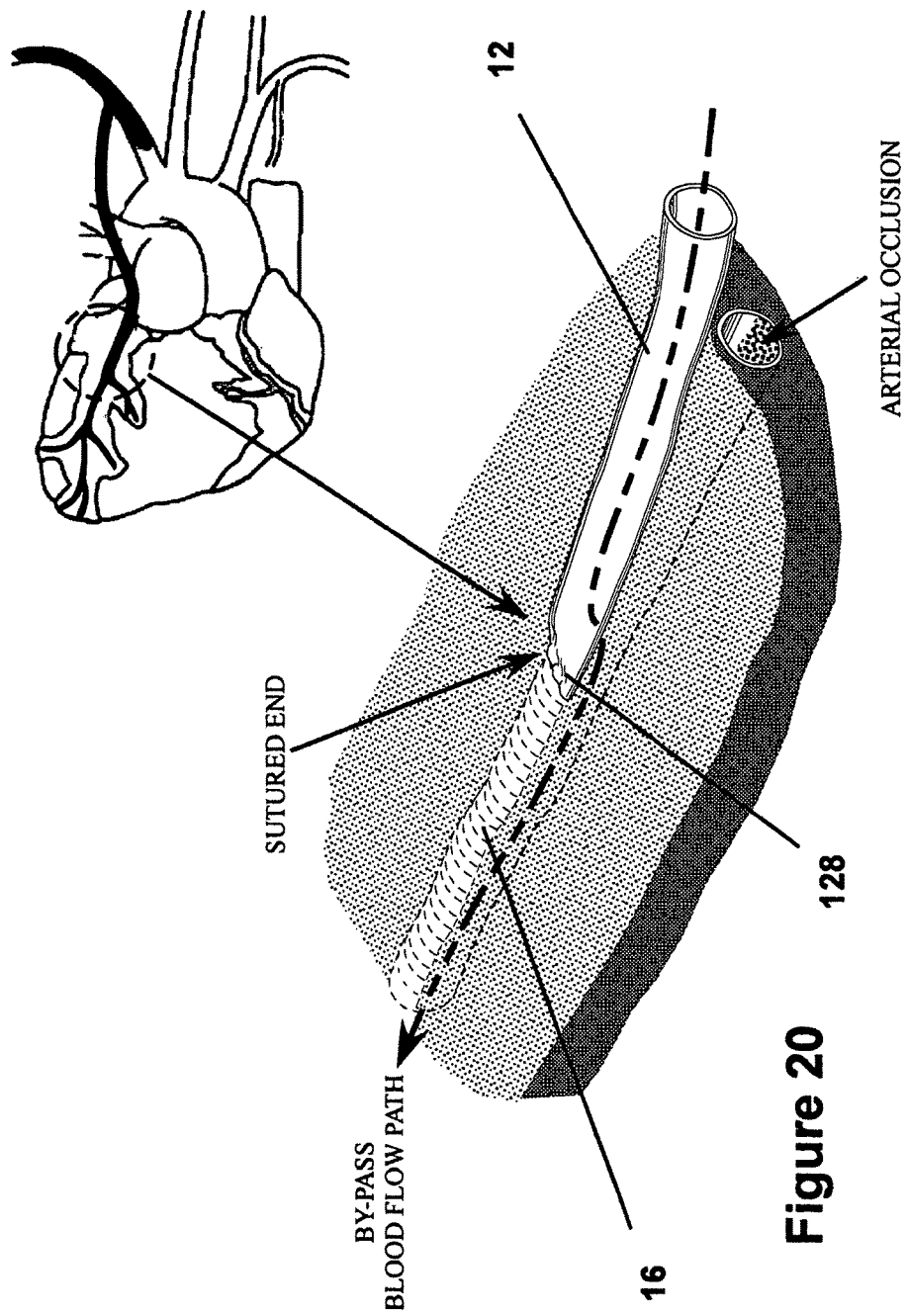
FIG. 20 is a perspective view of the graft shown attached to the heart wall with an end of the graft sutured closed.
Figure 26:
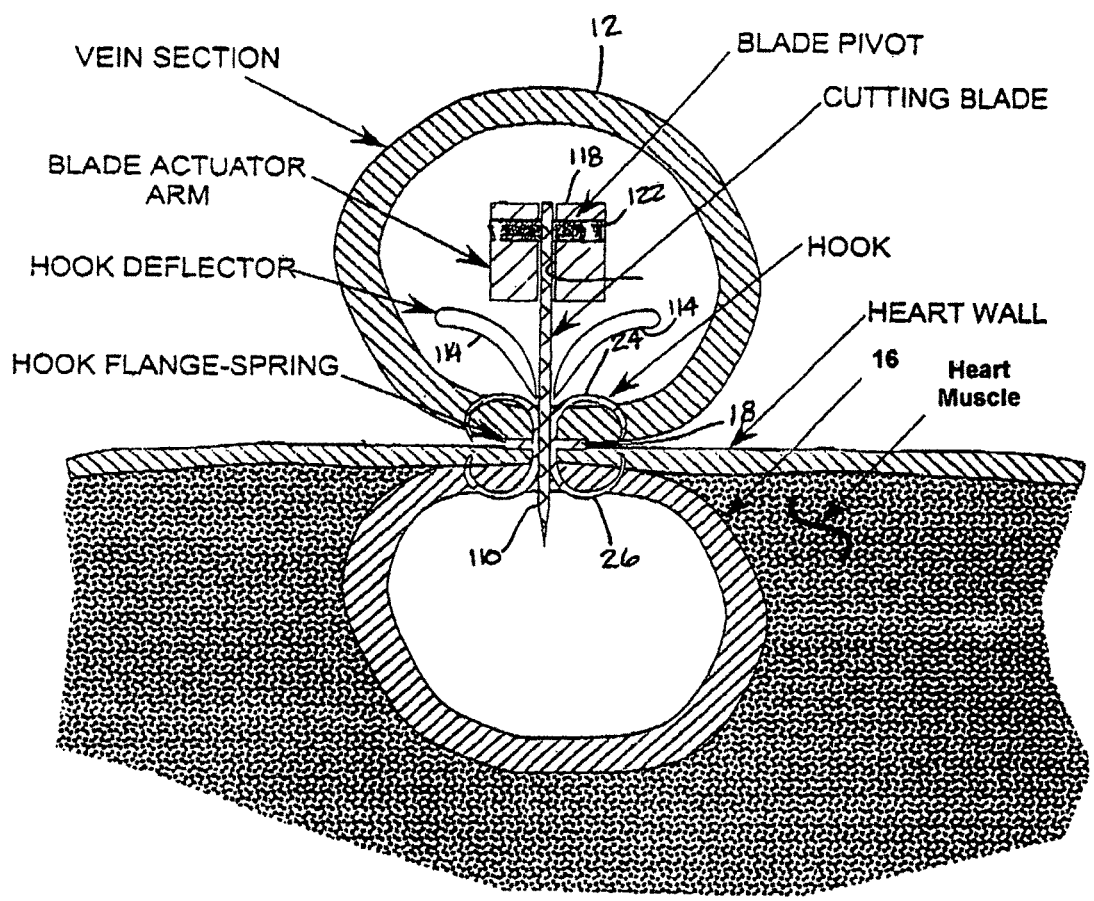
FIG. 26 is a view similar to FIG. 25 with the cutting mechanism shown in an initial cutting position.
Figure 27:
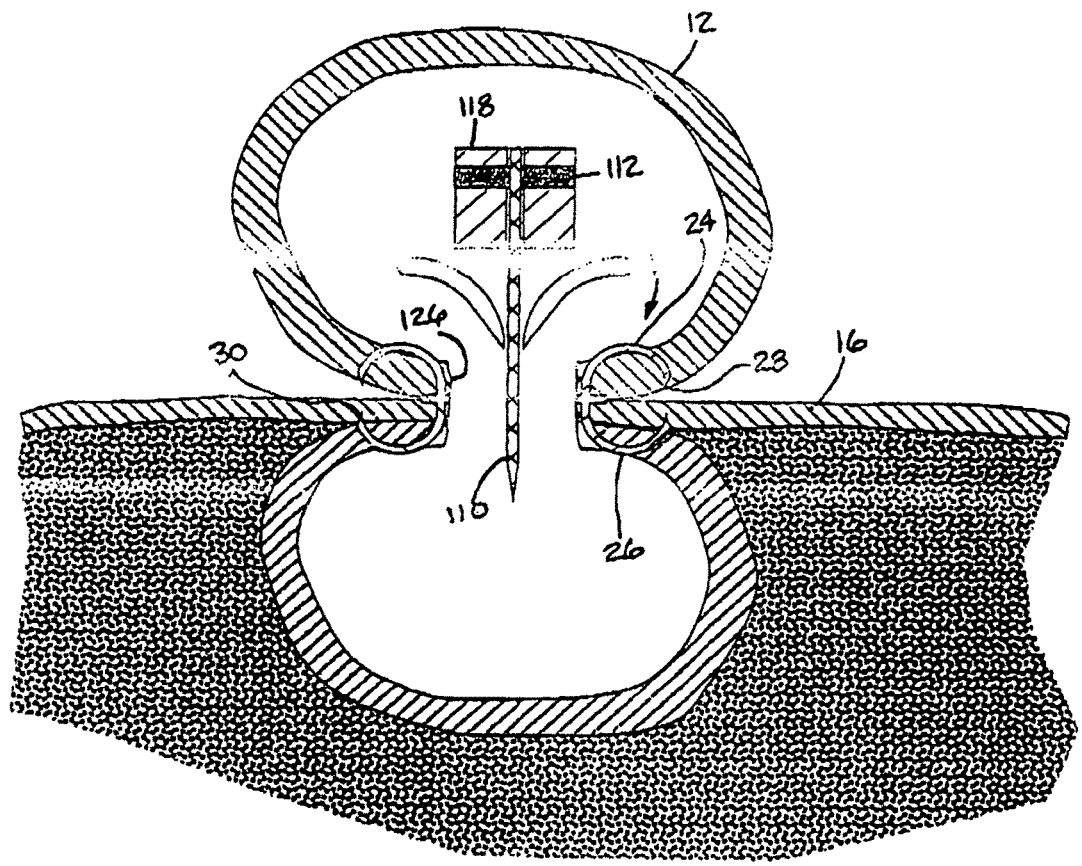
FIG. 27 is a view similar to FIG. 26 with the cutting mechanism shown in a final cutting position.
Figure 28:
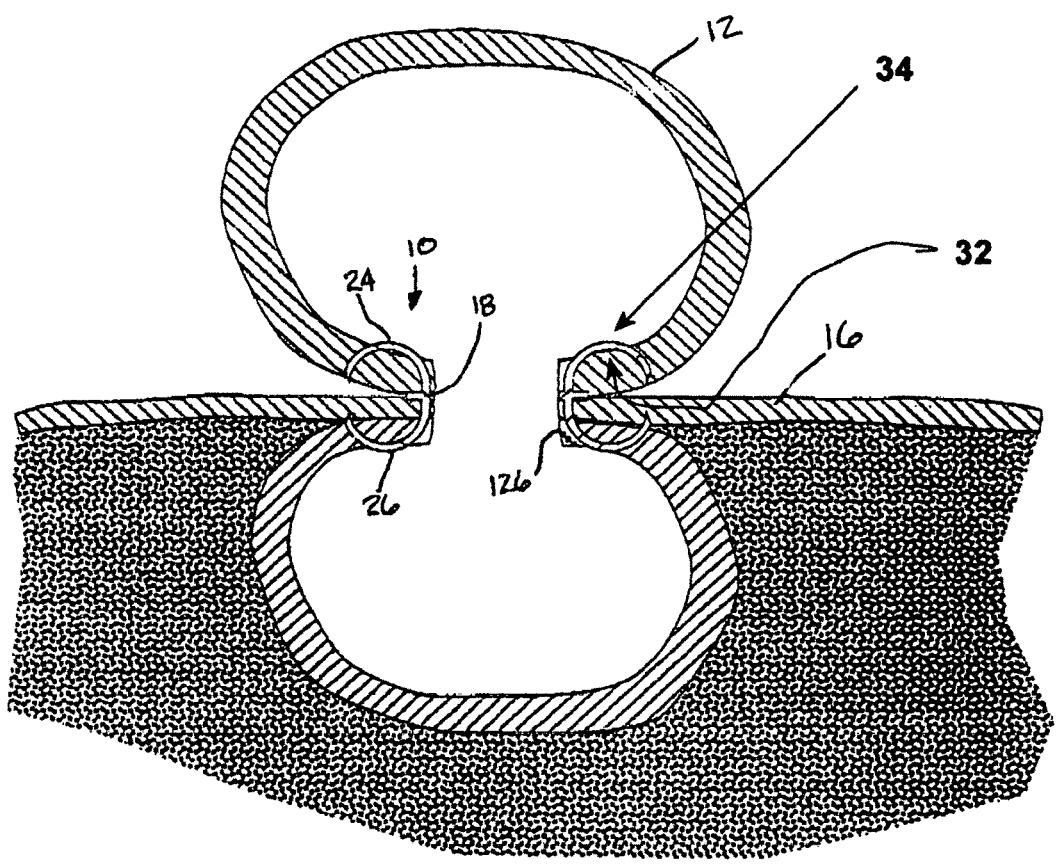
FIG. 28 is an enlarged cross-sectional view showing the fastener apparatus fully deployed to form an anastomosis between a side wall of the tubular duct and the heart wall to provide blood flow between the tubular graft and an artery underlying the heart wall.

As shown in FIGS. 19 and 26, the cutter 110 is then pivoted to its cutting position about the pin 122 by depressing the lever or trigger, thereby moving a cutting tip of the cutter 110 into a cutting position. The cutter 110 is then actuated by pulling the actuator rod 118, thereby causing the cutter 110 to traverse along the receptacle 76 via guided movement facilitated by the cutter slots 108 in the flanges 106 to form an incision through the graft 12 and the underlying tissue vessel 16, with the cutter 110 extending between the opposite sides of the annulus 18 and through the cutter channel 92 in the main body 74. Upon completion of the incision, as shown in FIGS. 27 and 28, the fastener apparatus 10 is generally free to assume its unbiased state, thereby establishing an opening 126 between the joined graft 12 and underlying tissue vessel 16 to provide blood flow through the opening 126. As shown in FIG. 20, the end of the graft 12 is then closed off, such as by a purse string suture 126, for example.

Figure 29:
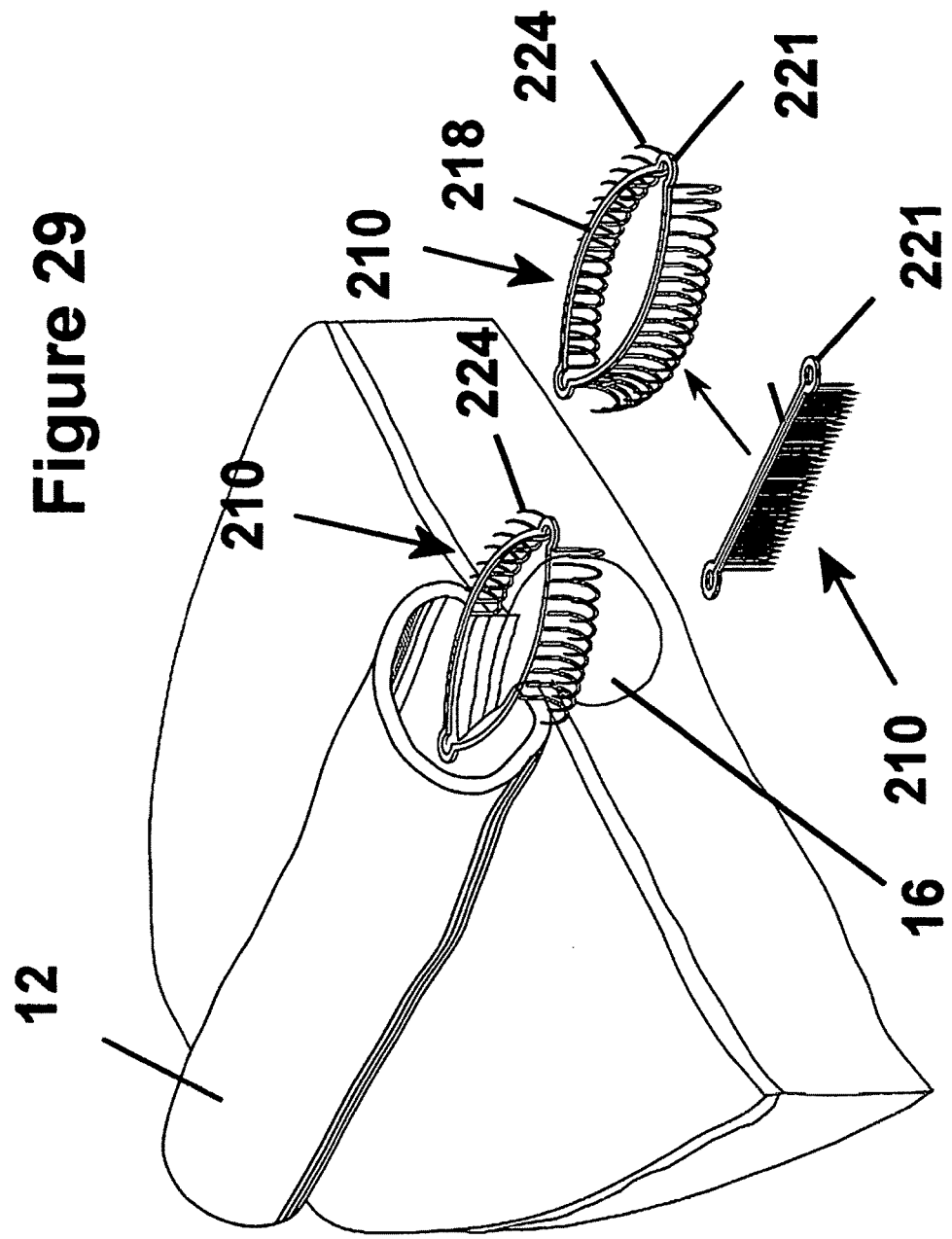
FIG. 29 is a broken away perspective view showing a fastener apparatus constructed according to another presently preferred embodiment of the invention attaching a tubular duct to a heart wall providing a blood flow path between the tubular duct and an artery underlying the heart wall.
Figure 30:
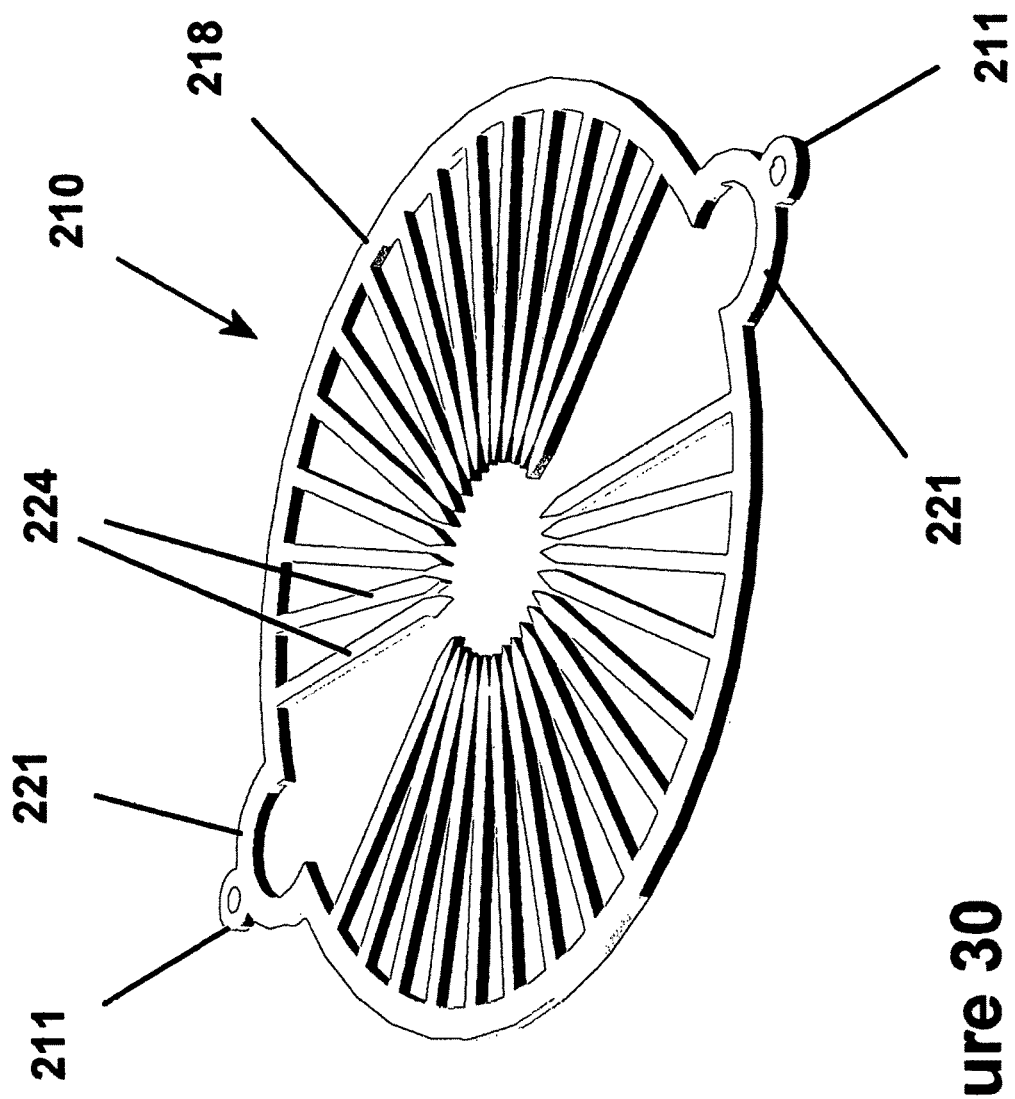
FIG. 30 is a perspective view of the fastener apparatus of FIG. 29 in a preformed state of construction.

In FIG. 29, another fastener apparatus 210 constructed according to another preferred embodiment of the invention is shown making a generally tangential anastomosis between a generally tubular duct 12 and a wall 14 of a vessel 16. The fastener apparatus 210 has an annulus 218 constructed generally the same as the annulus 18 in the first embodiment, with a first set of fingers 224 extending axially in one direction from the annulus 218. The fingers 224 are constructed generally the same as the first or second sets of fingers 24, 26 in the first embodiment, and thus are not described in further detail. As shown in FIG. 30, the fastener apparatus 210 has a generally similar preformed configuration as the fastener apparatus 10 in the previous embodiment, however all of the fingers 224 are formed in the same axial direction, rather than alternating axial directions as in the previous embodiment. The apparatus 210 is shown in FIG. 30 having eyelets 211 extending laterally from a pair of loops 221 to facilitate threading a tagging suture 124, otherwise, the construction of the fastener apparatus 210 is the same, and is not discussed further.

Figure 31:
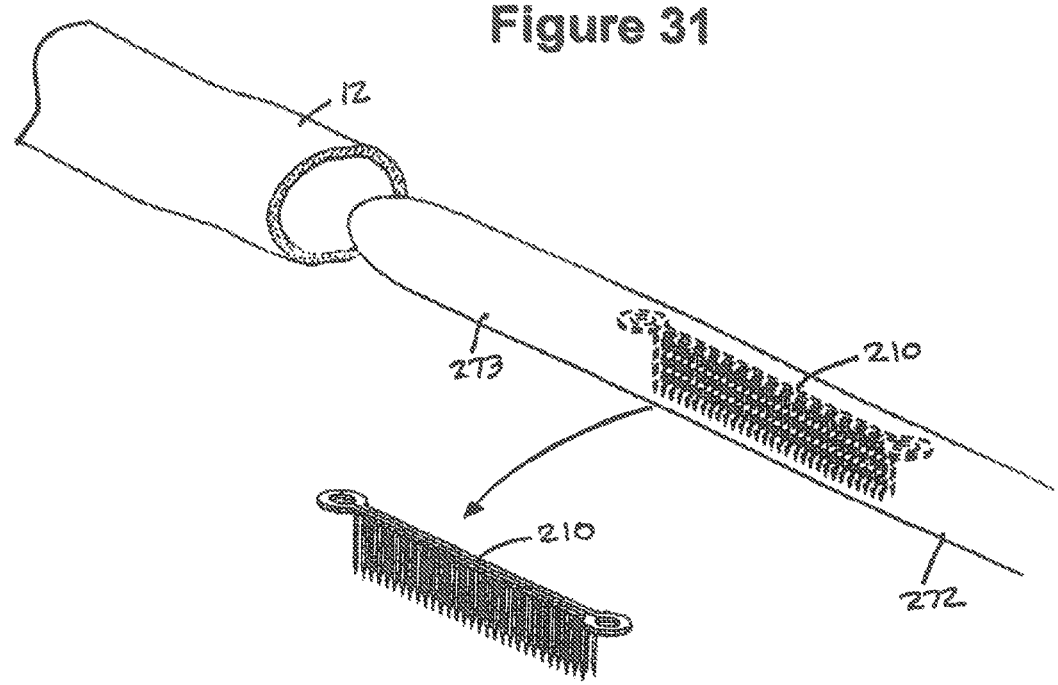
FIG. 31 is a perspective schematic view of the fastener apparatus of FIG. 29 shown in a biased state and being received within a receptacle of an alternate embodiment of a deployment apparatus for disposal within the tubular duct.
Figure 32:
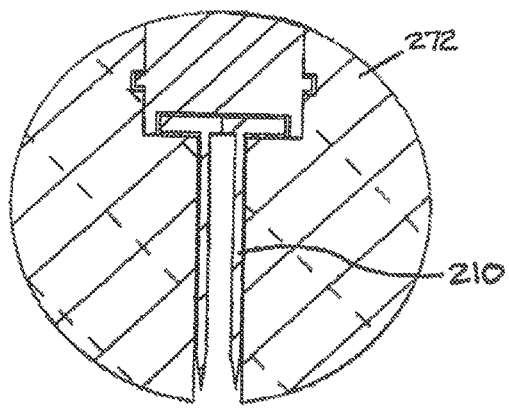
FIG. 32 is an enlarged cross sectional view of the fastener apparatus received within the deployment apparatus of FIG. 31.

In deployment, as shown generally in FIG. 31, a deployment apparatus 272 has a receptacle 273 sized for receipt within a selected tubular duct or graft 12. With the fastener apparatus 210 disposed in the receptacle 273 (FIG. 32), the fingers 224 are biased toward a flattened state (FIG. 31), as in the previous embodiment. Upon inserting the tubular duct 12 over the receptacle 273, and positioning the tubular duct 12 in the intended location of attachment relative to the tissue vessel 16, the fastener apparatus 210 is deployed generally similarly as in the previous embodiment, however, the annulus 218 is received internally to the graft 12, while the fingers 224 penetrate through a wall 215 of the graft 12 and into the adjoining tissue vessel 16. As such, the annulus 218 itself acts to partially bias the graft 12 into abutting contact with the underlying tissue vessel 16 by engaging an internal surface 217 of the graft wall 215. It should be recognized that the tagging suture 124 may also be used to facilitate attachment of the fastener apparatus 210, as in the previous embodiment. Because the annulus 218 itself acts to partially bias the graft 12 into abutting contact with the underlying tissue vessel 16, it may be desirable to may annulus 218 wider than annulus 18 so that there is more surface area on annulus 218 in contact with the tissue vessel 16. In this way, there is less of a chance that the annulus 218 will cut into the tissue of the tissue vessel 16.

As shown in FIG. 33, another embodiment of a fastener apparatus 310 has a discontinuous annulus 318. One end 312 of the annulus 318 has a generally hook shaped end, while another end 314 has a generally looped end sized for receipt of the hooked end 312. Otherwise, one or two sets of fingers (not shown) may extend axially from the annulus 318, as in the previous embodiments.

As shown in FIG. 34, another embodiment of a fastener apparatus 410 generally similar to the previous embodiment is shown, however, the apparatus 410 has a continuous loop of material forming an annulus 418. Opposite ends 412, 414 of the annulus 418 are preferably twisted to form loops 416 to facilitate guided attachment of the apparatus 410 by a tagging suture 124, as described above.

Figure 35:
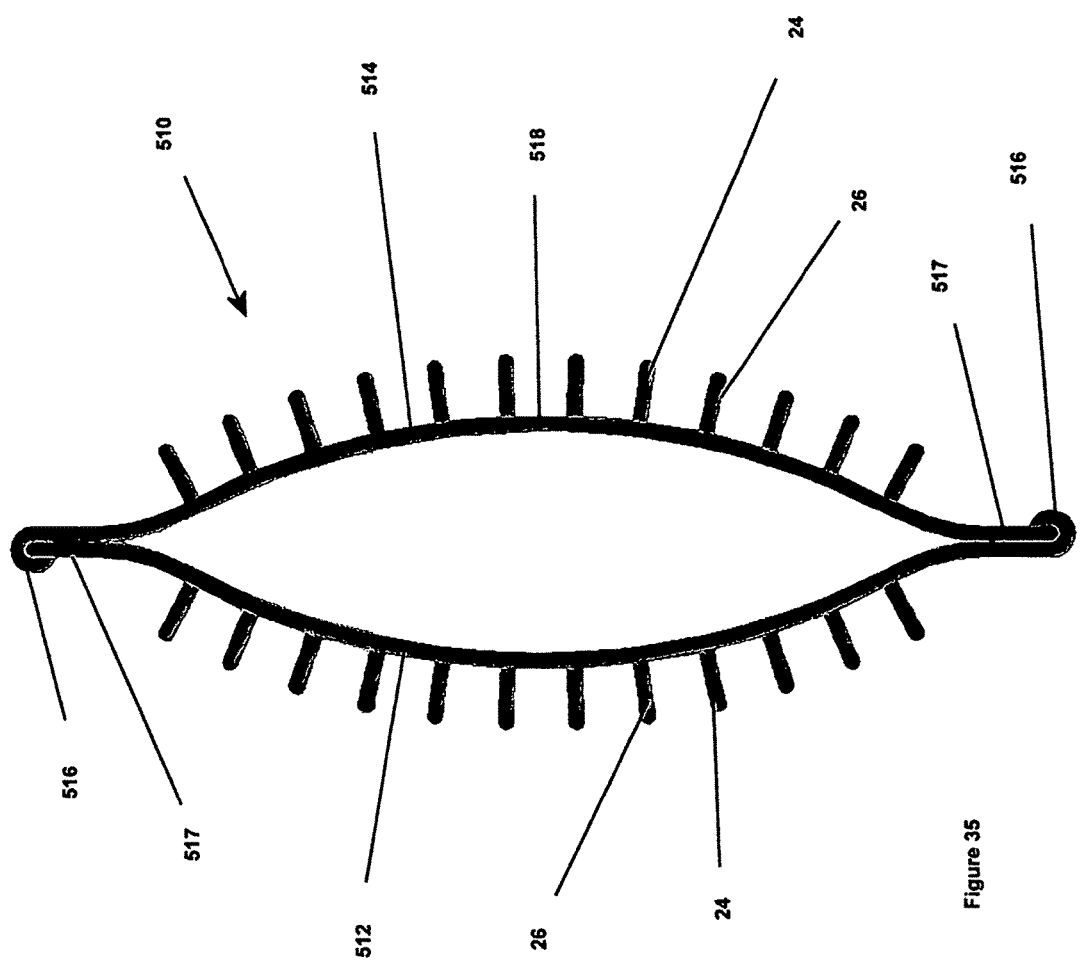
FIG. 35 is a bottom view of a fastener apparatus constructed according to another embodiment of the invention.

As shown in FIGS. 35 and 36, another presently preferred embodiment of a fastener apparatus 510 has an annulus 518 constructed from a pair of resilient springy wires 512, 514. Each wire 512, 514 has ends with one of a loop formation 516 and a hook formation 517, wherein the loops and hooks are arranged for attachment to an adjoining hook or loop on the opposite wire. It should be recognized that the annulus 518 may have one or two sets of fingers 24, 26, as described above, depending on the nature of the tissue connection.

As shown in FIG. 37, another presently preferred embodiment of the invention has an annulus 618 similar to the previous embodiment with first and second sets of fingers 624, 626 constructed from coiled spring wire. The first and second fingers 624, 626 are laterally spaced from one another by a coiled section 612 that defines a through opening 614 preferably sized for a tight fit about the annulus 618. The coiled section 612 may be defined by a plurality of coils to space the fingers 624, 626 laterally from one another, or the coil can be formed by a single coil, thereby locating the first and second fingers 624, 626 adjacent one another. As such, the number of first and second fingers 624, 626 may be altered or tailored for the specific type of anastomosis being formed. It should be recognized that the gage or diameter of spring wire may be altered, as desired. Otherwise, it should be recognized that the first and second fingers 624, 626 can be generally constructed the same as described above.

It is to be understood that the embodiments discussed above are exemplary embodiments of the presently preferred constructions, and thus are intended to be illustrative and not limiting. The scope of the invention is defined by the following claims.

The invention claimed is:

1. A method for deploying a fastener to secure a tubular duct having a wall to a vessel having a wall in a side by side configuration, comprising:
    constraining a first set of fingers of the fastener in substantially coplanar relation with one another with a deployment apparatus to move the first set of fingers into a biased state;
    disposing the constrained fastener between the tubular duct and vessel;
    releasing the constrained first set of fingers to allow the first set of fingers to assume a relaxed, unbiased shape and penetrate and grasp one of the tubular duct and vessel so that the fastener grasps and fixes the tubular duct and vessel to each other; and
    further including forming an opening within at least one of the tubular duct and vessel after releasing the constrained first set of fingers to allow blood to flow through the opening by extending a cutting member on the deployment apparatus between the first set of fingers and cutting tissue of the at least one of the tubular duct and vessel with the cutting member.

2. The method of claim 1 further including constraining a second set of fingers of the fastener in substantially coplanar relation with one another with the deployment apparatus to move the second set of fingers into a biased state and releasing the constrained second set of fingers to allow the second set of fingers to assume a relaxed, unbiased shape and penetrate and grasp the other one of the tubular duct and vessel.

3. The method of claim 2 further including biasing the first and second sets of fingers into a substantially coplanar relation with one another while constraining the first and second sets of fingers.

4. The method of claim 3 further including allowing the first and second sets of fingers to take on an arcuate heat-shaped configuration upon releasing the constrained fastener from the deployment apparatus.

* * * * *